United States Patent
Taniguchi et al.

(10) Patent No.: US 12,251,077 B2
(45) Date of Patent: Mar. 18, 2025

(54) SENSOR-EQUIPPED HOOD AND ENDOSCOPE

(71) Applicant: NISSHA CO., LTD., Kyoto (JP)

(72) Inventors: Chuzo Taniguchi, Kyoto (JP); Ryomei Omote, Kyoto (JP); Junichi Shibata, Kyoto (JP); Yoshiro Fujii, Kyoto (JP); Ryoma Tanimoto, Kyoto (JP)

(73) Assignee: NISSHA CO., LTD., Kyoto (JP)

( * ) Notice: Subject to any disclaimer, the term of this patent is extended or adjusted under 35 U.S.C. 154(b) by 0 days.

(21) Appl. No.: 18/713,130

(22) PCT Filed: Dec. 27, 2022

(86) PCT No.: PCT/JP2022/048296
§ 371 (c)(1),
(2) Date: May 23, 2024

(87) PCT Pub. No.: WO2023/181576
PCT Pub. Date: Sep. 28, 2023

(65) Prior Publication Data
US 2024/0415371 A1    Dec. 19, 2024

(30) Foreign Application Priority Data
Mar. 25, 2022 (JP) .................. 2022-049744

(51) Int. Cl.
*A61B 1/00* (2006.01)
(52) U.S. Cl.
CPC ...... *A61B 1/00057* (2013.01); *A61B 1/00089* (2013.01); *A61B 1/00097* (2022.02)

(58) Field of Classification Search
CPC ............ A61B 1/00057; A61B 1/00089; A61B 1/00097; A61B 1/009
See application file for complete search history.

(56) References Cited

U.S. PATENT DOCUMENTS

| | | | |
|---|---|---|---|
| 2008/0285909 A1 | 11/2008 | Younge et al. | |
| 2010/0249506 A1* | 9/2010 | Prisco | A61B 1/0051 600/117 |
| 2012/0289777 A1* | 11/2012 | Chopra | A61B 1/009 382/128 |
| 2022/0304559 A1* | 9/2022 | Weeks | A61B 1/0655 |

FOREIGN PATENT DOCUMENTS

| | | |
|---|---|---|
| JP | 2007089733 A | 4/2007 |
| JP | 2011030735 A | 2/2011 |
| JP | 2019522228 A | 8/2019 |
| WO | 2021176530 A1 | 9/2021 |

* cited by examiner

Primary Examiner — Aaron B Fairchild
(74) Attorney, Agent, or Firm — Alleman Hall & Tuttle LLP

(57) ABSTRACT

To provide a sensor-equipped hood capable of detecting force applied to the hood without narrowing an operating field viewed through the hood. A sensor-equipped hood protrudes from a tip end portion of an endoscope main body, and is attached to the tip end portion. The sensor-equipped hood includes a transparent tubular hood main body and a fiber Bragg grating (FBG) sensor fixed to a first fixing point of the hood main body and having a Bragg grating. In the FBG sensor, the wavelength of reflected light at the Bragg grating changes based on fluctuation of the first fixing point in the hood main body.

11 Claims, 28 Drawing Sheets

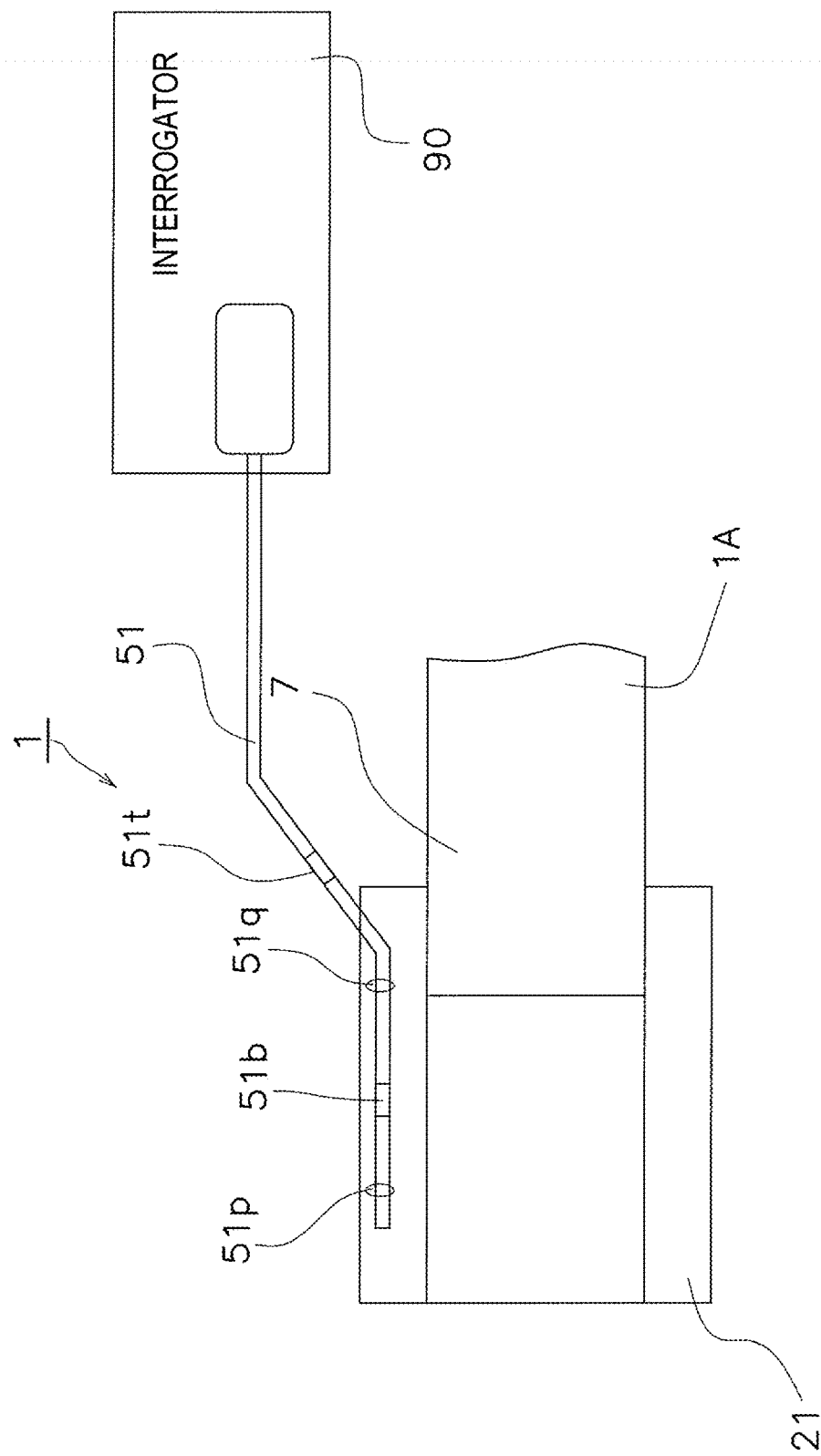

SENSOR-EQUIPPED HOOD AND ENDOSCOPE

TECHNICAL FIELD

The present invention relates to a sensor-equipped hood attached to a tip end portion of an endoscope and an endoscope including the sensor-equipped hood.

BACKGROUND ART

A transparent hood for protecting a tip end portion of an endoscope currently frequently used is attached to the tip end portion of the endoscope. The hood of the endoscope may actively contact and act on a human body in a surgery using the endoscope. Even in such a case, an operating field viewed through the hood is an important information source for the surgery.

CITATION LIST

Patent Literature

Patent Literature 1: JP2011-30735A

SUMMARY OF INVENTION

Problems to be Solved by Invention

In the field of the endoscope, for example, it has been proposed to detect the shape of an insertion portion of an endoscope using a fiber Bragg grating sensor as described in Patent Literature 1 (JP2011-30735A).

However, even if the sensor is attached to the endoscope as in Patent Literature 1, it is difficult to detect force applied to the hood of the endoscope from, e.g., the human body. Thus, it is conceivable to attach the sensor to the hood, but in a case where the sensor is attached to the hood, it is important not to narrow the operating field viewed through the hood.

An object of the present invention is to provide a sensor-equipped hood capable of detecting force applied to the hood without narrowing an operating field viewed through the hood.

Solution to Problems

Hereinafter, a plurality of aspects will be described as means for solving the problem. These aspects can be arbitrarily combined as necessary.

A sensor-equipped hood according to one aspect of the present invention is a sensor-equipped hood protruding from a tip end portion of an endoscope main body and attached to the tip end portion. The sensor-equipped hood includes a transparent tubular hood main body and a fiber Bragg grating sensor fixed to a first fixing point of the hood main body and having a Bragg grating. In the fiber Bragg grating sensor, the wavelength of reflected light at the Bragg grating changes based on fluctuation of the first fixing point in the hood main body. The sensor-equipped hood having such a configuration can detect fluctuation of the first fixing point in the hood main body by detecting the change in the wavelength of the reflected light at the fiber Bragg grating sensor. Stress applied to the hood main body can be detected from fluctuation of the first fixing point while narrowing of an operating field obtained through the hood main body is reduced.

In the above-described sensor-equipped hood, the fiber Bragg grating sensor may be fixed at a second fixing point in the hood main body, the Bragg grating may be arranged between the first fixing point and the second fixing point, and the wavelength of the reflected light at the Bragg grating may change according to a change in an interval between the first fixing point and the second fixing point. The sensor-equipped hood configured as described above can measure, by the fiber Bragg grating sensor, the stress changing the interval between the first fixing point and the second fixing point.

In the above-described sensor-equipped hood, the first fixing point may include a first point, the second fixing point may include a second point, and the Bragg grating may include a first Bragg grating. In the fiber Bragg grating sensor, the first point and the second point may be arranged at positions apart from each other in the axial direction of the hood main body, the first Bragg grating may be arranged between the first point and the second point, and the wavelength of reflected light at the first Bragg grating may change according to a change in an interval between the first point and the second point. The sensor-equipped hood configured as described above can measure, by the fiber Bragg grating sensor, the stress applied between the first point and the second point in the axial direction of the hood main body, such as the compressive stress and the tensile stress in the axial direction of the hood main body.

In the above-described sensor-equipped hood, the first fixing point may include a third point, the second fixing point may include a fourth point, and the Bragg grating may include a second Bragg grating. In the fiber Bragg grating sensor, the third point and the fourth point may be arranged apart from each other in the axial direction on a second straight line different from a first straight line connecting the first point and the second point, the second Bragg grating may be arranged between the third point and the fourth point, and the wavelength of reflected light at the second Bragg grating may change according to a change in an interval between the third point and the fourth point. The sensor-equipped hood configured as described above can measure the stress applied between the first point and the second point and the stress applied between the third point and the fourth point in the axial direction of the hood main body and strain at different locations. In other words, for example, the bending stress applied to the hood main body can be measured.

In the above-described sensor-equipped hood, the first fixing point may include a fifth point, the second fixing point may include a sixth point, and the Bragg grating may include a third Bragg grating. In the fiber Bragg grating sensor, the fifth point and the sixth point may be arranged at positions apart from each other in the circumferential direction of the hood main body, the third Bragg grating may be arranged between the fifth point and the sixth point, and the wavelength of reflected light at the second Bragg grating may change according to a change in an interval between the third point and the fourth point. The sensor-equipped hood configured as described above can measure the stress applied between the fifth point and the sixth point in the circumferential direction of the hood main body, such as the tensile stress or the compressive stress in the radial direction of the hood main body.

In the above-described sensor-equipped hood, the first fixing point may include a seventh point, the second fixing point may include an eighth point, and the Bragg grating may include a fourth Bragg grating. In the fiber Bragg grating sensor, the seventh point and the eighth point may be arranged at positions apart from each other in the circumferential direction of the hood main body, the fourth Bragg grating may be arranged between the seventh point and the eighth point, the wavelength of reflected light at the fourth Bragg grating may change according to a change in an interval between the seventh point and the eighth point, and the third Bragg grating and the fourth Bragg grating may be arranged in a first optical fiber and a second optical fiber different from each other in a winding direction. The sensor-equipped hood configured as described above can measure not only the stress applied between the fifth point and the sixth point in the circumferential direction of the hood main body in the first optical fiber but also the stress applied between the seventh point and the eighth point in the circumferential direction of the hood main body in the second optical fiber different from the first optical fiber in the winding direction, and can measure, for example, the force for twisting the hood main body.

In the above-described sensor-equipped hood, in the fiber Bragg grating sensor, a plurality of Bragg gratings may be arranged in one optical fiber, and a plurality of first fixing points may be arranged corresponding to the Bragg gratings. In the sensor-equipped hood configured as described above, the number of optical fibers can be reduced while the number of measurement points is increased.

In the above-described sensor-equipped hood, the fiber Bragg grating sensor may be fitted in a hole or a groove formed in the hood main body, and may be fixed to the first fixing point by pressure applied from the hood main body to the fiber Bragg grating sensor or an adhesive. By removing the pressure applied to the fiber Bragg grating sensor, the fiber Bragg grating sensor can be unfixed, and separation between the hood main body and the fiber Bragg grating sensor is facilitated.

In the above-described sensor-equipped hood, the hood main body may include an outer tube and an inner peripheral portion arranged in contact with the inside of the outer tube, and the fiber Bragg grating sensor may be arranged between the outer tube and the inner peripheral portion. In the sensor-equipped hood configured as described above, the fiber Bragg grating sensor is easily attached to the hood main body by using the outer tube and the inner peripheral portion.

An endoscope according to one aspect of the present invention includes an endoscope main body, a hood main body, a fiber Bragg grating sensor, and an interrogator. The hood main body is a transparent tubular body attached to a tip end portion of the endoscope main body. The fiber Bragg grating sensor is fixed to a first fixing point of the hood main body, and has a Bragg grating. The interrogator measures the stress related to fluctuation of the first fixing point in the hood main body by the reflected light at the Bragg grating of the fiber Bragg grating sensor. In such an endoscope, the stress applied to the hood main body can be detected by the fiber Bragg grating sensor while narrowing of an operating field obtained through the hood main body is reduced.

Effects of Invention

In the sensor-equipped hood or the endoscope according to the present invention, the stress applied to the hood main body can be detected by the fiber Bragg grating sensor while narrowing of the operating field obtained through the hood main body is reduced.

BRIEF DESCRIPTION OF DRAWINGS

FIG. 8 is a schematic view for describing a measurement method using a hood-equipped sensor.

DESCRIPTION OF EMBODIMENTS (1) Overall Configuration of Endoscope

Figure 1:
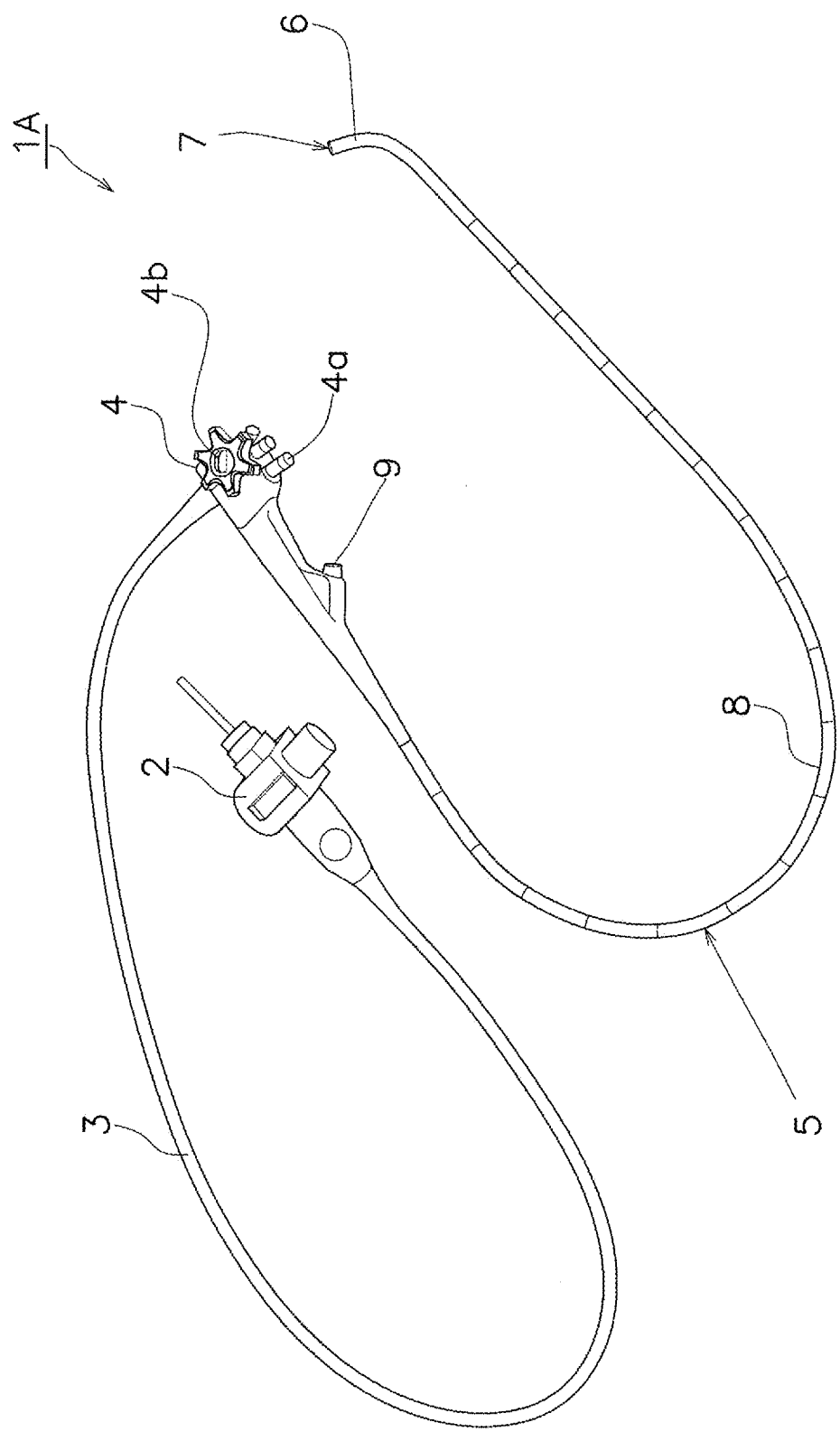
FIG. 1 is a perspective view illustrating one example of an endoscope main body.

FIG. 1 illustrates one example of the appearance of an endoscope main body 1A. The endoscope main body 1A includes a connector 2 and a universal cord 3 for connection with a device main body (not illustrated). The main body has a function of sending, for example, water and air through a monitor (not illustrated) that displays an image captured by the endoscope main body 1A and the universal cord 3. The universal cord 3 is provided with a pipeline (not illustrated) for sending water and air and a signal cable (not illustrated) for transmitting captured image data.

The endoscope main body 1A includes an operator 4 for operation and an insertion portion 5 to be inserted into a body. A curved portion 6 and a tip end portion 7 are located at the tip of the insertion portion 5, and the operator 4 and the curved portion 6 are connected to each other by a flexible portion 8. The operator 4 is provided with a button 4a such as a suction button, an air/water sending button, and a shutter button. By operating the button 4a, the endoscope main body 1A performs, e.g., operations of sending air, sending water, and performing suction through the insertion portion 5. In addition, by operating the button 4a related to imaging, such as the shutter button, e.g., a shutter and an illumination can be operated.

An angle knob 4b of the operator 4 is connected to the tip end portion 7 of the endoscope main body 1A with a wire (not illustrated). By operating the angle knob 4b, the endoscope main body 1A can bend the curved portion 6 in various directions (for example, up, down, left, and right), and can direct the tip end portion 7 in various directions. Since the curved portion 6 can be bent, the endoscope main body 1A can be used not only to facilitate insertion of the insertion portion 5 into the body, but also to observe the inside of a body cavity at 360 degrees.

A forceps channel 9 is located in the vicinity of the operator 4. The forceps channel 9 is used for taking in and out a treatment tool. For example, forceps inserted through the forceps channel 9 can be sent to the tip end portion 7. The treatment tool is not only carried into the body through the inside of the insertion portion 5, but also carried into the body using, for example, a guide tube (not illustrated) provided on the surface of the insertion portion 5. In this manner, the treatment tool carried through the outside of the insertion portion 5 passes outside of a hood main body 21 (see FIGS. 3 and 4) to be described later. Since the hood main body 21 is transparent, the treatment tool passing outside of the hood main body 21 can also be viewed through the hood main body 21.

Figure 2:
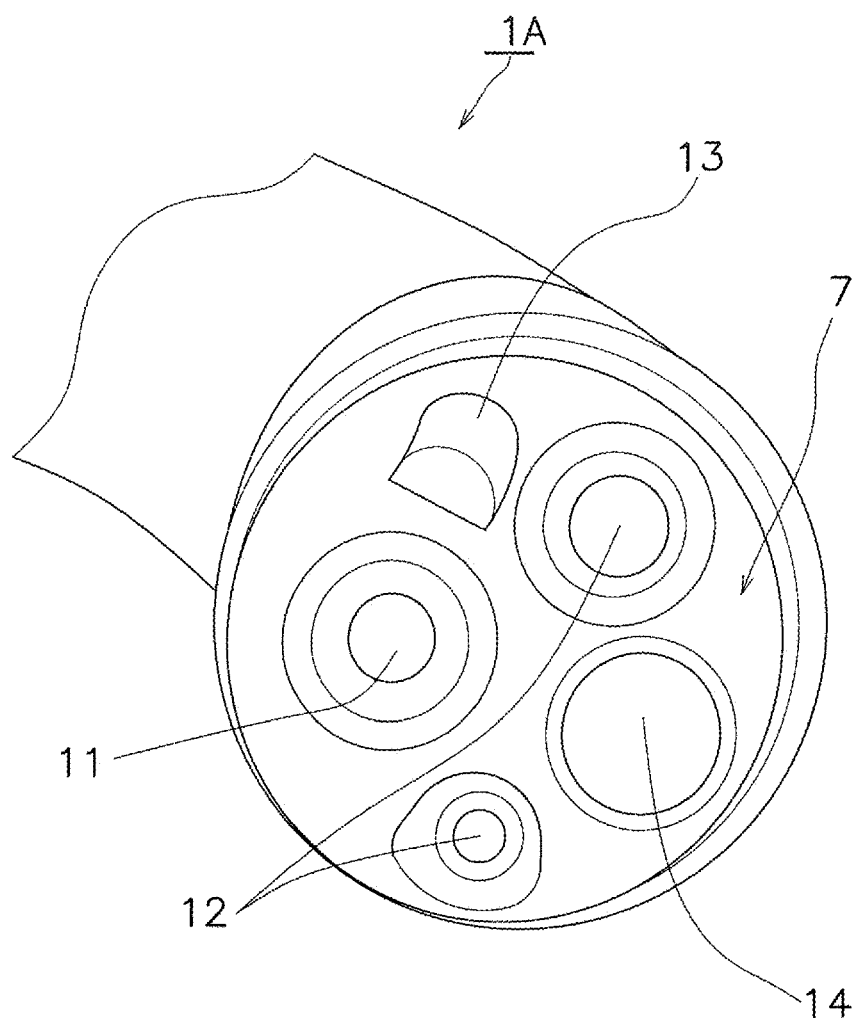
FIG. 2 is a partially enlarged perspective view illustrating a tip end portion of the endoscope main body in closeup.

As illustrated in FIG. 2, the tip end portion 7 of the endoscope main body 1A is provided with, for example, an objective lens 11, a light guide lens 12, an air/water sending nozzle 13, and a forceps inlet/outlet port 14. A CCD image sensor (not illustrated) is arranged inside the objective lens 11. An image captured by the CCD image sensor is displayed on the monitor connected to the connector 2 and provided on the device main body.

(2) Hood (2-1) Form of Hood

Figure 3:
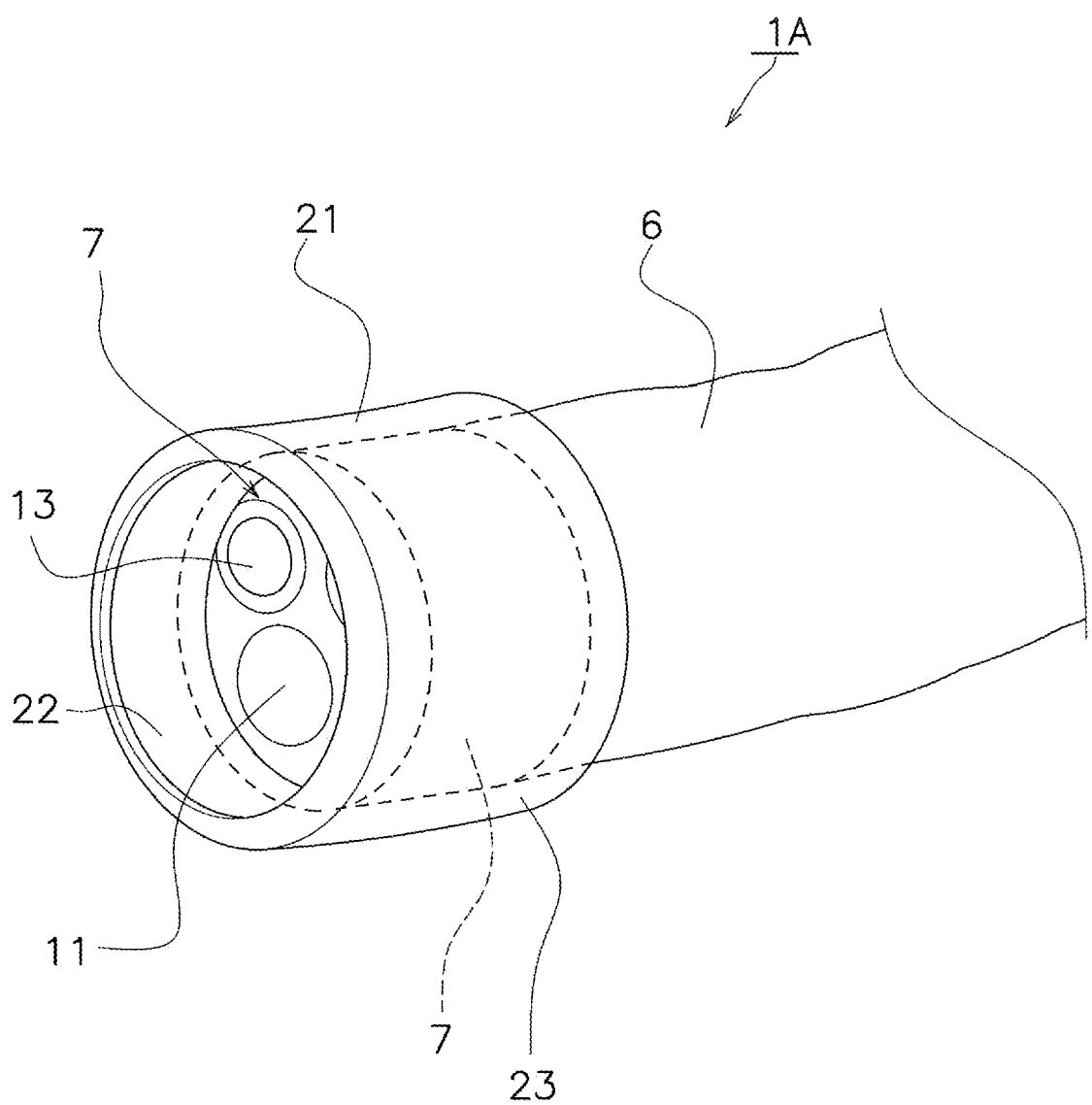
FIG. 3 is a partially enlarged perspective view illustrating the tip end portion of the endoscope main body in closeup.

As illustrated in FIG. 3, the hood main body 21 is attached to the tip end portion 7 of the endoscope main body 1A. The hood main body 21 is a transparent tubular body. In order to obtain the transparent hood main body 21, a transparent polymer material is used as the material of the hood main body 21. Examples of the transparent polymer material include transparent resin and transparent elastomer. Examples of the transparent resin or transparent elastomer used for the hood main body 21 include polycarbonate and silicone. The shape of the hood main body 21 is a tubular shape, and examples of a sectional shape perpendicular to the axis of the tubular shape include a circular shape, an elliptical shape, and a quadrangular shape. In the tubular hood main body 21, the size of the sectional shape perpendicular to the axis may be changed along the axis. In other words, the surface of the tubular hood main body 21 may have a frustum shape. In the tubular hood main body 21, the sectional shape perpendicular to the axis may be changed along the axis. For example, the sectional shape of a front portion of the hood main body 21 may be an elliptical shape, and the sectional shape of a back portion may be a circular shape. The front portion of the hood main body 21 may be obliquely cut.

Figure 4:
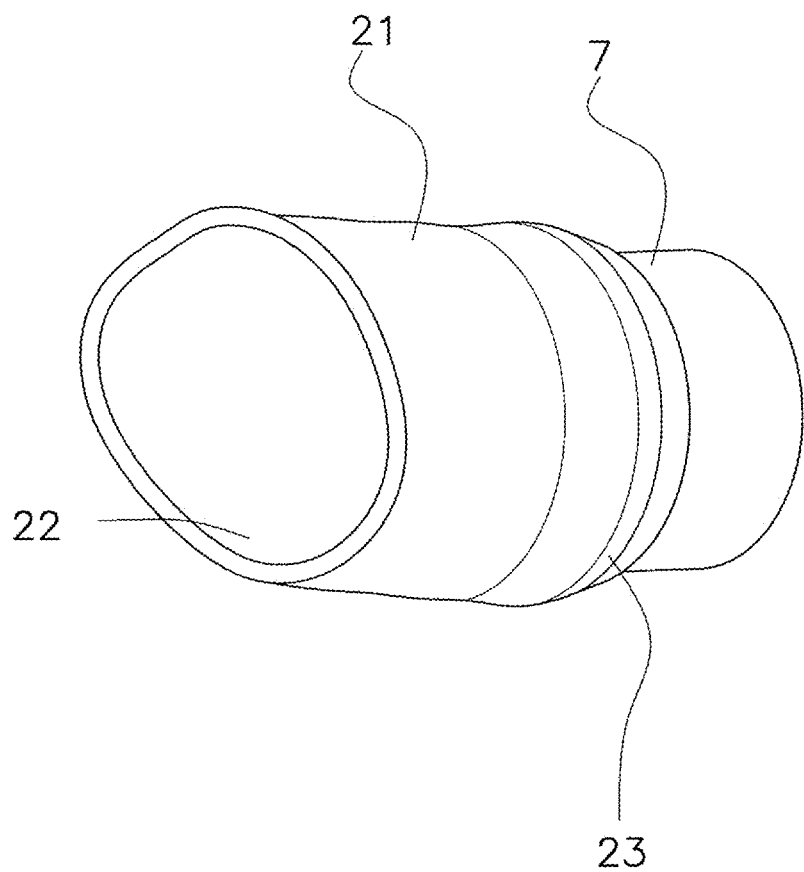
FIG. 4 is a perspective view illustrating the appearance of a hood main body.

As illustrated in FIGS. 3 and 4, the hood main body 21 has a protruding portion 22 protruding from the tip end portion 7 and an attachment portion 23 attached to the tip end portion 7. In the hood main body 21, the protruding portion 22 and the attachment portion 23 may be made of different materials. For example, the protruding portion 22 may be made of polycarbonate, and the attachment portion 23 may be made of silicone.

The protruding portion 22 of the hood main body 21 has, for example, an outer diameter of 3 mm to 15 mm and a length of 2 mm to 15 mm. The thickness of the protruding portion 22 is about 0.5 mm to 2 mm.

(2-2) Stress Applied to Hood

Figure 5A:
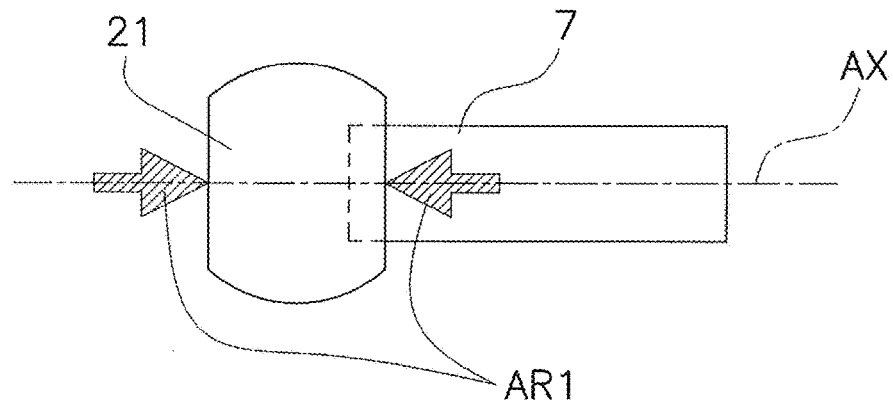
FIG. 5A is a conceptual view for describing compressive stress in the axial direction of the hood main body.
Figure 5B:
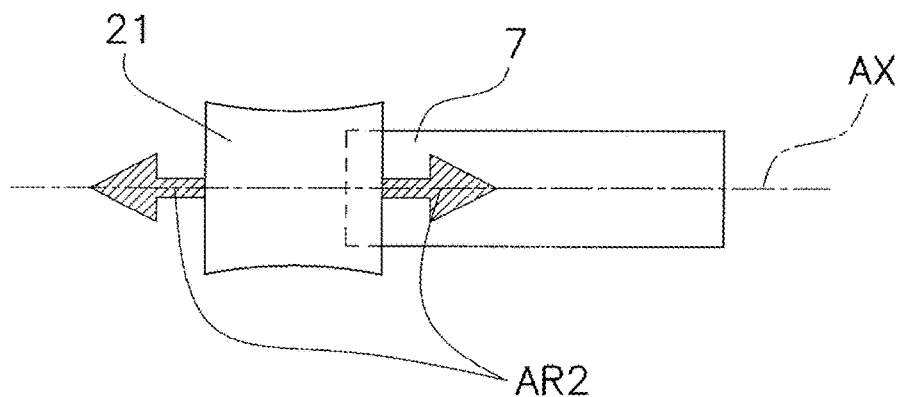
FIG. 5B is a conceptual view for describing tensile stress in the axial direction of the hood main body.
Figure 5C:
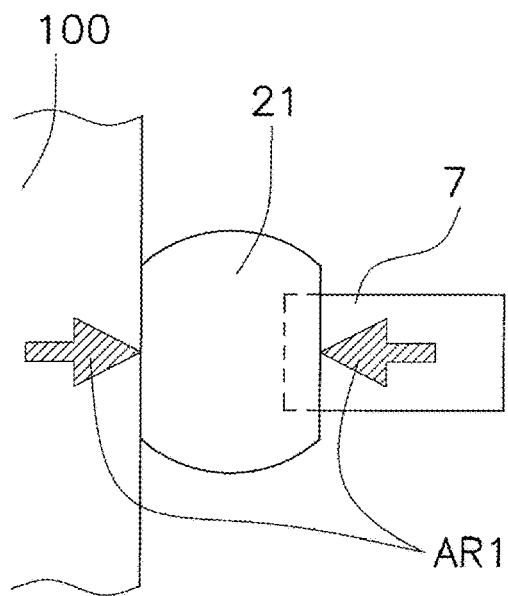
FIG. 5C is a conceptual view for describing a situation where the compressive stress is generated on the hood main body.

FIGS. 5A, 5B, 5C, 6A, and 6B illustrate examples of stress applied to the hood main body 21. FIG. 5A illustrates the state of the hood main body 21 in a case where force (compressive stress) in the direction of arrows AR1 is applied. FIG. 5B illustrates the state of the hood main body 21 in a case where force (tensile stress) in the direction of arrows AR2 is applied. FIG. 5C illustrates force applied to the hood main body 21 when the hood main body 21 hits a portion 100 of the human body. The force applied when the hood main body 21 hits the portion 100 of the human body is compressive stress. For example, in a case where the endoscope main body 1A is inserted into the large intestine and pushes folds aside, the compressive stress is applied to the tip end of the hood main body 21. The directions of the arrows AR1 and the arrows AR2 are directions along an axis AX of the hood main body 21. In other words, the compressive stress in the direction of the arrows AR1 is compressive stress in the axial direction, and the tensile stress in the direction of the arrows AR2 is tensile stress in the axial direction.

Figure 6A:
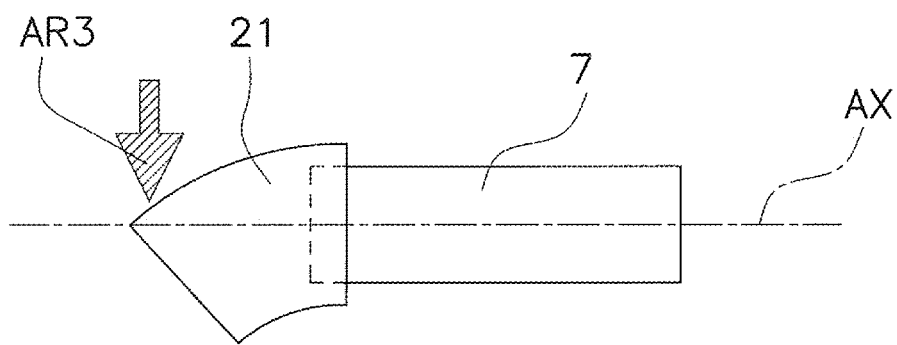
FIG. 6A is a conceptual view for describing bending stress on the hood main body.
Figure 6B:
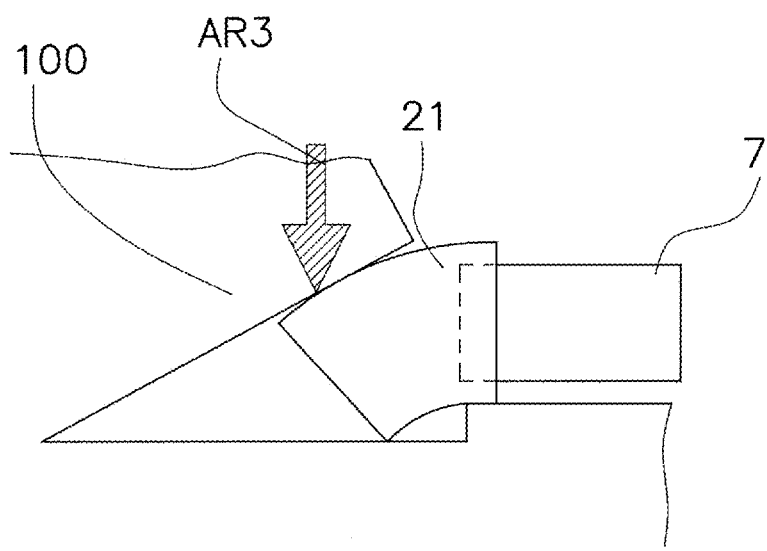
FIG. 6B is a conceptual view for describing a situation where the bending stress is generated on the hood main body.

FIG. 6A illustrates the state of the hood main body 21 in a case where force (bending stress) in the direction of an arrow AR3 is applied to bend the hood main body 21. The direction of the arrow AR3 is a direction perpendicular to the axis AX of the hood main body 21. FIG. 6B illustrates force applied to the hood main body 21 when the hood main body 21 lifts the portion 100 of the human body. For example, during an endoscopic submucosal dissection (ESD) procedure, the hood main body 21 may be located under the submucosa which is the portion 100 of the human body. At this time, force for bending the hood main body 21 is applied from the submucosa. Here, a typical example of the stress applied to the hood main body 21 is illustrated, but in an actual surgery, force is applied to the hood main body 21 in a complex manner. For example, in the ESD, when the hood main body 21 is inserted into the portion 100 of the human body, not only the bending stress but also the compressive stress is assumed to be applied.

(2-3) Fiber Bragg Grating Sensor and Arrangement Thereof

Figure 7:
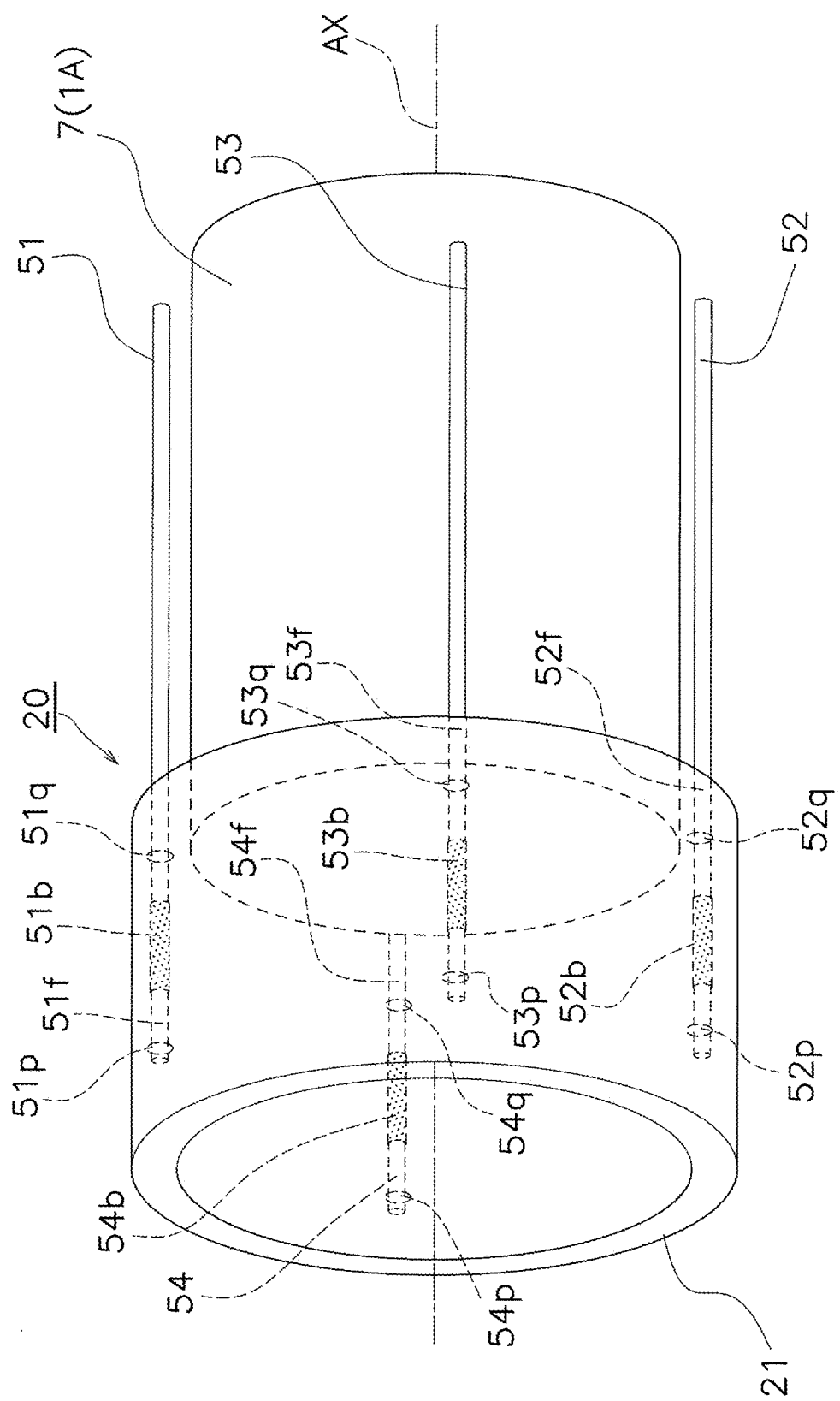
FIG. 7 is a perspective view illustrating one example of a sensor-equipped hood.

In the following description, a fiber Bragg grating sensor will be referred to as an FBG sensor. FIG. 7 illustrates a sensor-equipped hood 20 in which four FBG sensors 51, 52, 53, 54 are arranged. The FBG sensors 51, 52, 53, 54 and the hood main body 21 form the sensor-equipped hood 20. The FBG sensors 51 to 54 are transparent and have water resistance. The FBG sensors 51 to 54 are made of quartz glass, and include optical fibers 51f, 52f, 53f, 54f having an outer diameter of about 0.2 mm, for example. Since the FBG sensors 51 to 54 are very thin and transparent, the influence of the FBG sensors 51 to 54 is extremely small in a case where the portion 100 of the human body is observed through the hood main body 21.

The claddings of the optical fibers 51f to 54f are, for example, about 0.1 mm. The total length of the optical fibers 51f to 54f is, for example, about 2 m. Part of the optical fibers 51f to 54f of the FBG sensors 51 to 54 is inserted into the hood main body 21. The optical fibers 51f to 54f extend in parallel with the axis AX in the hood main body 21. Bragg gratings 51b, 52b, 53b, 54b of the FBG sensors 51, 52, 53, 54 are arranged in the hood main body 21. In the optical fibers 51f to 54f, for example, the lengths of the Bragg gratings 51b to 54b is about 2 mm.

The optical fiber 51f is fixed to the hood main body 21 at a first fixing point 51p in front of the Bragg grating 51b and a second fixing point 51q in back of the Bragg grating 51b. The Bragg grating 51b is not fixed to the hood main body 21. The first fixing point 51p and the second fixing point 51q may have certain lengths instead of having a point-like shape. In other words, the optical fiber 51f may be fixed at the first fixing point 51p and the second fixing point 51q such that the optical fiber 51f and the hood main body 21 are joined to each other so as not to be separated in a linear region. A method of fixing the optical fiber 51f may be a physical fixing method such as screwing, fitting, clamping, taping, wedging, or caulking, or may be a chemical fixing method such as an adhesive. Similarly, the optical fiber 52f, 53f, 54f is fixed to the hood main body 21 at a first fixing point 52p, 53p, 54p in front of the Bragg grating 52b, 53b, 54b and a second fixing point 52q, 53q, 54q in back of the Bragg grating 52b, 53b, 54b. The Bragg gratings 51b to 54b are preferably arranged on the protruding portion 22 rather than on the attachment portion 23 because the stress can be more easily measured with higher accuracy at the protruding portion 22 at which the hood main body 21 is not influenced by the tip end portion 7.

In the FBG sensor 51, the wavelength of reflected light at the Bragg grating 51b changes based on fluctuation of the first fixing point 51p in the hood main body 21. Similarly, in the FBG sensor 52, 53, 54, the wavelength of reflected light at the Bragg grating 52b, 53b, 54b changes based on fluctuation of the first fixing point 52p, 53p, 54p in the hood main body 21. Based on such a change in the wavelength, the force applied to the hood main body 21 can be measured.

More specifically, when the compressive stress in the axial direction as illustrated in FIG. 5C is applied to the hood main body 21, an interval between the first fixing point 51p, 52p, 53p, 54p and the second fixing point 51q, 52q, 53q, 54q arranged at positions apart from each other in the axial direction decreases. When the interval between the first fixing point 51p, 52p, 53p, 54p and the second fixing point 51q, 52q, 53q, 54q decreases, the interval of the Bragg grating 51b, 52b, 53b, 54b also decreases, and the wavelength of the reflected light at the Bragg grating 51b, 52b, 53b, 54b changes.

When the tensile stress in the axial direction as illustrated in FIG. 5B is applied to the hood main body 21, the interval between the first fixing point 51p, 52p, 53p, 54p and the second fixing point 51q, 52q, 53q, 54q arranged at the positions apart from each other in the axial direction increases. When the interval between the first fixing point 51p, 52p, 53p, 54p and the second fixing point 51q, 52q, 53q, 54q increases, the interval of the Bragg grating 51b, 52b, 53b, 54b also increases, and the wavelength of the reflected light at the Bragg grating 51b, 52b, 53b, 54b changes.

In the above-described case, the first fixing point 51p, 52p, 53p, 54p can be taken as a first point, the second fixing point 51q, 52q, 53q, 54q can be taken as a second point, and the FBG sensor 51, 52, 53, 54 can be taken as one configured such that the first point and the second point are at positions apart from each other in the axial direction of the hood main body 21. In addition, the Bragg grating 51b, 52b, 53b, 54b can be taken as a first Bragg grating arranged between the first point and the second point.

When the bending stress as illustrated in FIG. 6A is applied from the FBG sensor 51 to the FBG sensor 52 of the hood main body 21, the interval between the first fixing point 51p and the second fixing point 51q increases, and the interval between the first fixing point 52p and the second fixing point 52q decreases. When the interval between the first fixing point 51p and the second fixing point 51q increases, the interval of the Bragg grating 51b also increases, and the wavelength of the reflected light at the Bragg grating 51b changes. Conversely, when the interval between the first fixing point 52p and the second fixing point 52q decreases, the interval of the Bragg grating 52b also decreases, and the wavelength of the reflected light at the Bragg grating 52b changes. In this manner, since the wavelength transitions in an opposite manner between the FBG sensor 51 and the FBG sensor 52, it is possible to detect that the bending stress has been applied.

In the above-described case, for example, the first fixing point 51p can be taken as a first point, the second fixing point 51q can be taken as a second point, the first fixing point 52p can be taken as a third point, the second fixing point 52q can be taken as a fourth point, and the FBG sensor 51, 52 can be taken as one arranged on a second straight line different from a first straight line connecting the first point and the second point and configured such that the third point and the fourth point are apart from each other in the axial direction. In this case, the first straight line is taken as a straight line overlapping with the optical fiber 51f in the hood main body 21, and the second straight line is taken as a straight line overlapping with the optical fiber 52f in the hood main body 21. In this case, the Bragg grating 51b can be regarded as a first Bragg grating arranged between the first point and the second point, and the Bragg grating 52b can be regarded as a second Bragg grating arranged between the third point and the fourth point.

(2-4) Measurement System Using FBG Sensor

FIG. 8 illustrates the outline of a measurement system using the FBG sensor 51. The FBG sensors 52 to 54 described with reference to FIG. 7 will not be illustrated and described. The front side of the FBG sensor 51 is inserted into the hood main body 21 as described with reference to FIG. 7. The back side of the FBG sensor 51 is connected to an interrogator 90. A Bragg grating 51t for temperature compensation is provided outside the hood main body 21. The Bragg gratings 51b, 51t have diffraction grating periods different from each other. Thus, the wavelengths of the reflected light at the Bragg gratings 51b, 51t are different from each other, and in the interrogator 90, the reflected light can be separately measured for the Bragg gratings 51b, 51t. In the Bragg grating 51t, the wavelength of the reflected light changes according to a temperature change. The temperature change is detected from the change in the wavelength of the reflected light at the Bragg grating 51t, and the wavelength change due to the temperature of the Bragg grating 51b is corrected.

An endoscope 1 illustrated in FIG. 8 includes the endoscope main body 1A, the transparent tubular hood main body 21 attached to the tip end portion 7 of the endoscope main body 1A, the FBG sensor 51 fixed to the first fixing point 51p of the hood main body 21 and having the Bragg grating 51b, and the interrogator 90 that measures stress related to fluctuation of the first fixing point 51p in the hood main body 21 by the reflected light from the Bragg grating 51b of the FBG sensor 51.

Here, a method of measuring the stress by the FBG sensor 51 has been described, but a measurement method similar to that of the FBG sensor 51 can also be applied to a case of using the FBG sensors 52s to 54.

Here, the FBG sensor 51 is connected from the interrogator 90 to the hood main body 21 through one line. However, the interrogator 90 and the hood main body 21 may be separable from each other by using a component, such as an optical connector, that optically connects the optical fiber 51f to an attachment portion of the hood main body 21.

(2-5) Method of Fixing FBG Sensor

One example of a method of fixing the FBG sensor 51 will be described with reference to FIGS. 9A and 9B. The hood main body 21 illustrated in FIGS. 9A and 9B includes a cylindrical transparent outer tube 21a and a cylindrical transparent inner tube 21b. A groove 21f for fitting the FBG sensor 51 therein is formed in an outer peripheral portion of the inner tube 21b. The outer tube 21a and the inner tube 21b are made of, for example, polycarbonate. The FBG sensor 51 set in the groove 21f of the inner tube 21b is inserted into the outer tube 21a. The outer tube 21a is deformed by a jig 201 from the outside of the outer tube 21a into which the inner tube 21b is inserted, and in this manner, the FBG sensor 51 is fixed. For example, the jig 201 applies temperature and pressure to spots corresponding to the first fixing point 51p and the second fixing point 51q to deform the outer tube 21a toward the inner tube 21b. Due to deformation of the outer tube 21a, the optical fiber 51f is fixed at the first fixing point 51p and the second fixing point 51q so as not to move in the axial direction. Note that in this case, the outer tube 21a is deformed after the inner tube 21b has been inserted into the outer tube 21a. However, before insertion of the inner tube 21b, for example, protrusions may be provided corresponding to the first fixing point 51p and the second fixing point 51q on the inner peripheral surface of the outer tube 21a, and the FBG sensor 51 may be fixed with these protrusions. Deformation of the inner tube 21b or the outer tube 21a for fixing the optical fiber 51f may be performed before the outer tube 21a is inserted into the inner tube 21b.

(3) Modifications (3-1) Modification A

In the above-described embodiment, the sensor-equipped hood 20 capable of measuring the compressive stress, the tensile stress, and the bending stress has been described. However, the stress to be measured by the sensor-equipped hood 20 is not limited to the above-described stress.

(3-1-1) Stress Applied to Hood

Figure 10A:
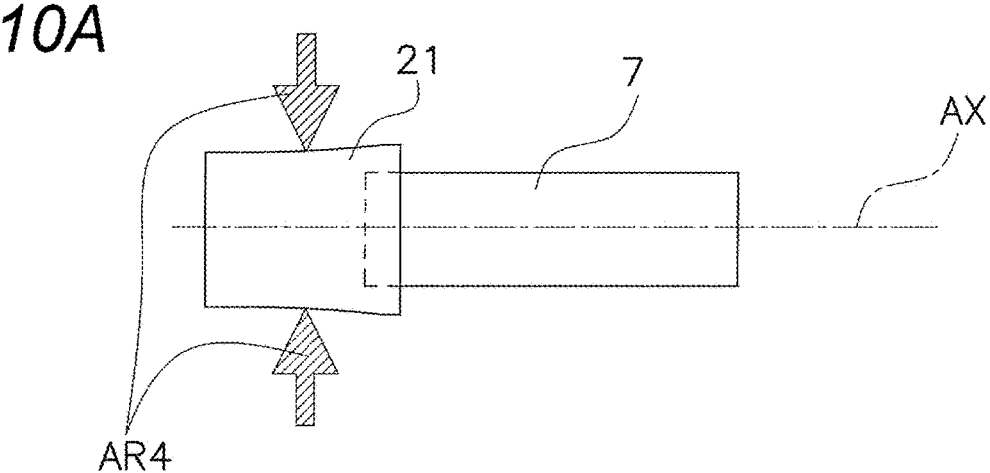
FIG. 10A is a conceptual view for describing compressive stress in the radial direction of the hood main body.
Figure 10B:
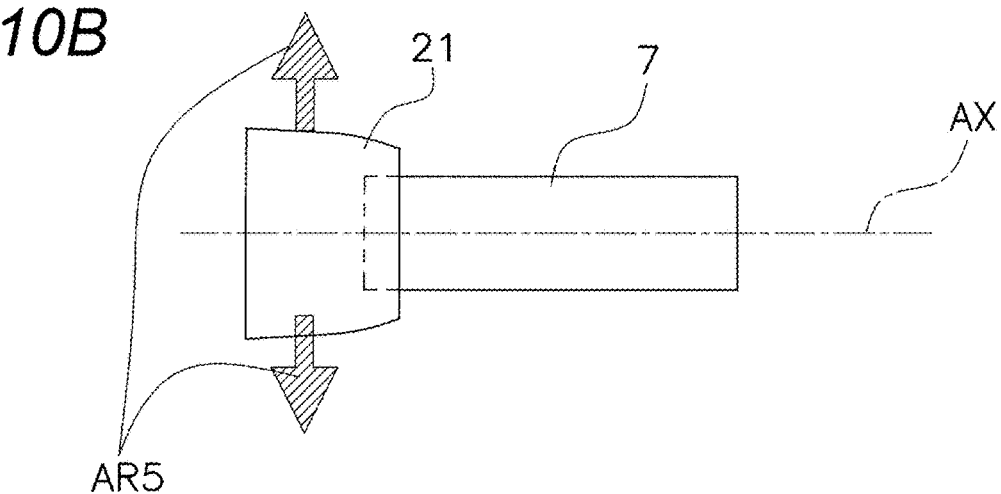
FIG. 10B is a conceptual view for describing tensile stress in the radial direction of the hood main body.
Figure 10C:
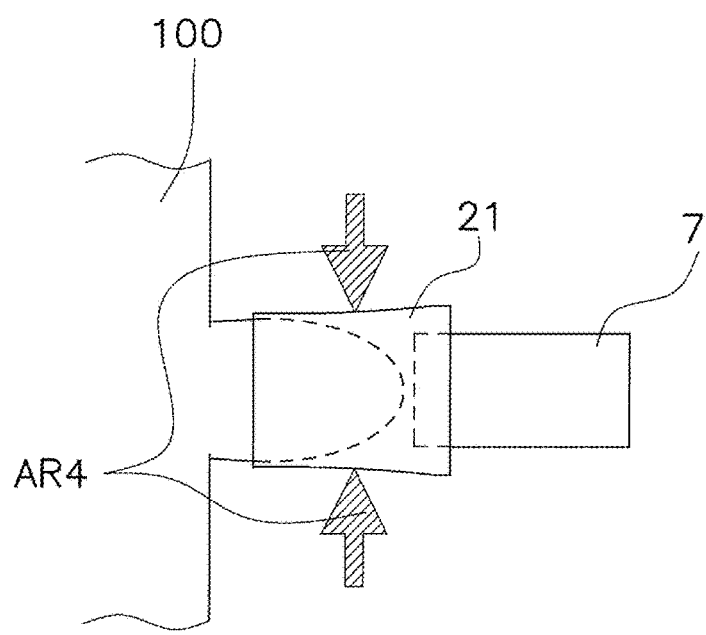
FIG. 10C is a conceptual view for describing a situation where the compressive stress in the radial direction of the hood main body is generated.

FIGS. 10A, 10B, and 10C illustrate examples of the stress applied to the hood main body 21. FIG. 10A illustrates the state of the hood main body 21 in a case where force (compressive stress) in the direction of arrows AR4 is applied. The compressive stress in the direction of the arrows AR4 is compressive stress in a radial direction. FIG. 10B illustrates the state of the hood main body 21 in a case where force (tensile stress) in the direction of arrows AR5 is applied. FIG. 10C illustrates force applied to the hood main body 21 when the hood main body 21 sucks the portion 100 of the human body. The force applied when the hood main body 21 sucks the portion 100 of the human body is compressive stress in the radial direction. For example, during an endoscopic aspiration mucosal resection (EMRC or EAM) procedure, the hood main body 21 sucks, into a cap (hood main body 21), a mucous membrane which is the portion 100 of the human body. At this time, the compressive stress in the radial direction is applied to the hood main body 21 by suction. Here, a typical example of the stress applied to the hood main body 21 is illustrated, but in an actual surgery, force is applied to the hood main body 21 in a complex manner. For example, in the EMRC, it is assumed that tensile stress in the axial direction is applied when the portion 100 of the human body is sucked.

Figure 11A:
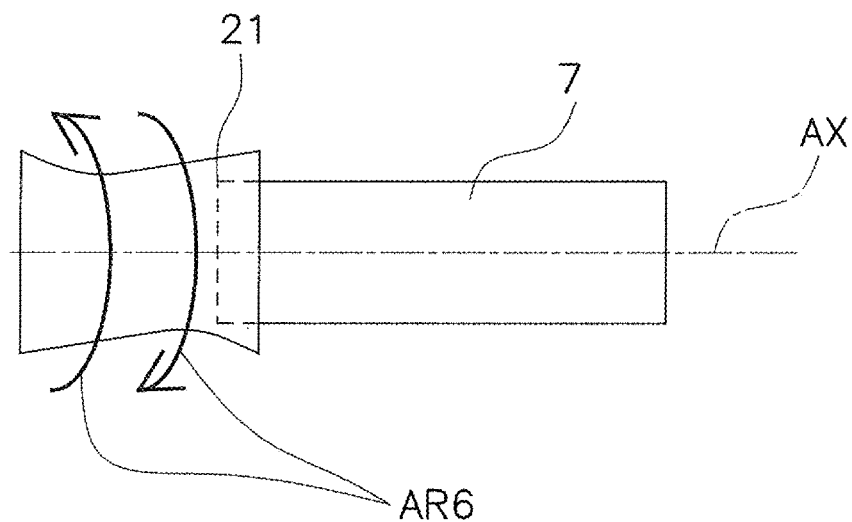
FIG. 11A is a conceptual view for describing torsional stress on the hood main body.
Figure 11B:
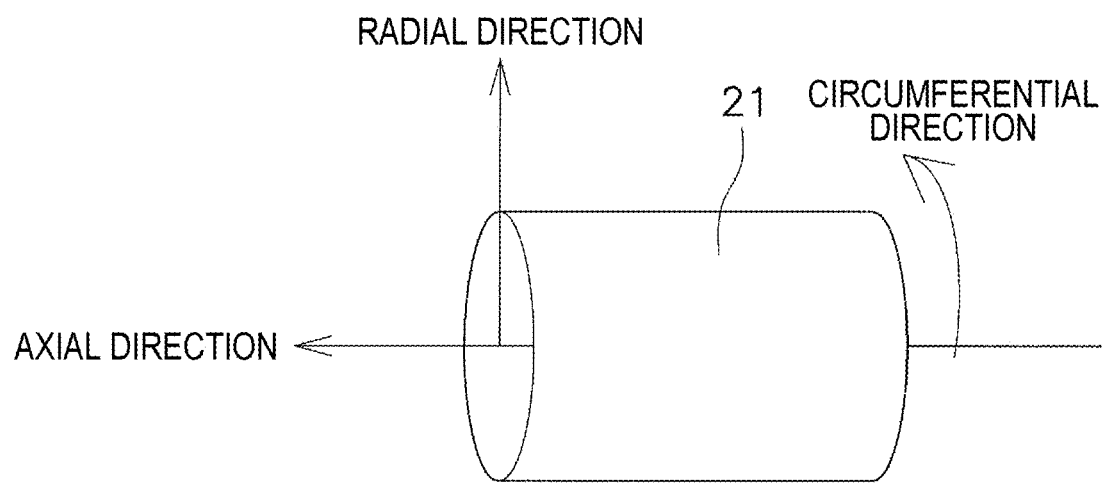
FIG. 11B is a conceptual view illustrating a relationship between the hood main body and a cylindrical coordinate system.

FIG. 11A illustrates the state of the hood main body 21 in a case where force (torsional stress) in the direction of arrows AR6 is applied to twist the hood main body 21. The force for twisting the hood main body 21 is force for rotating the hood main body 21 in the opposite directions about the axis AX. FIG. 11B illustrates one example of a cylindrical coordinate system applied to the hood main body 21.

(3-1-2) FBG Sensor and Arrangement Thereof.

Figure 12:
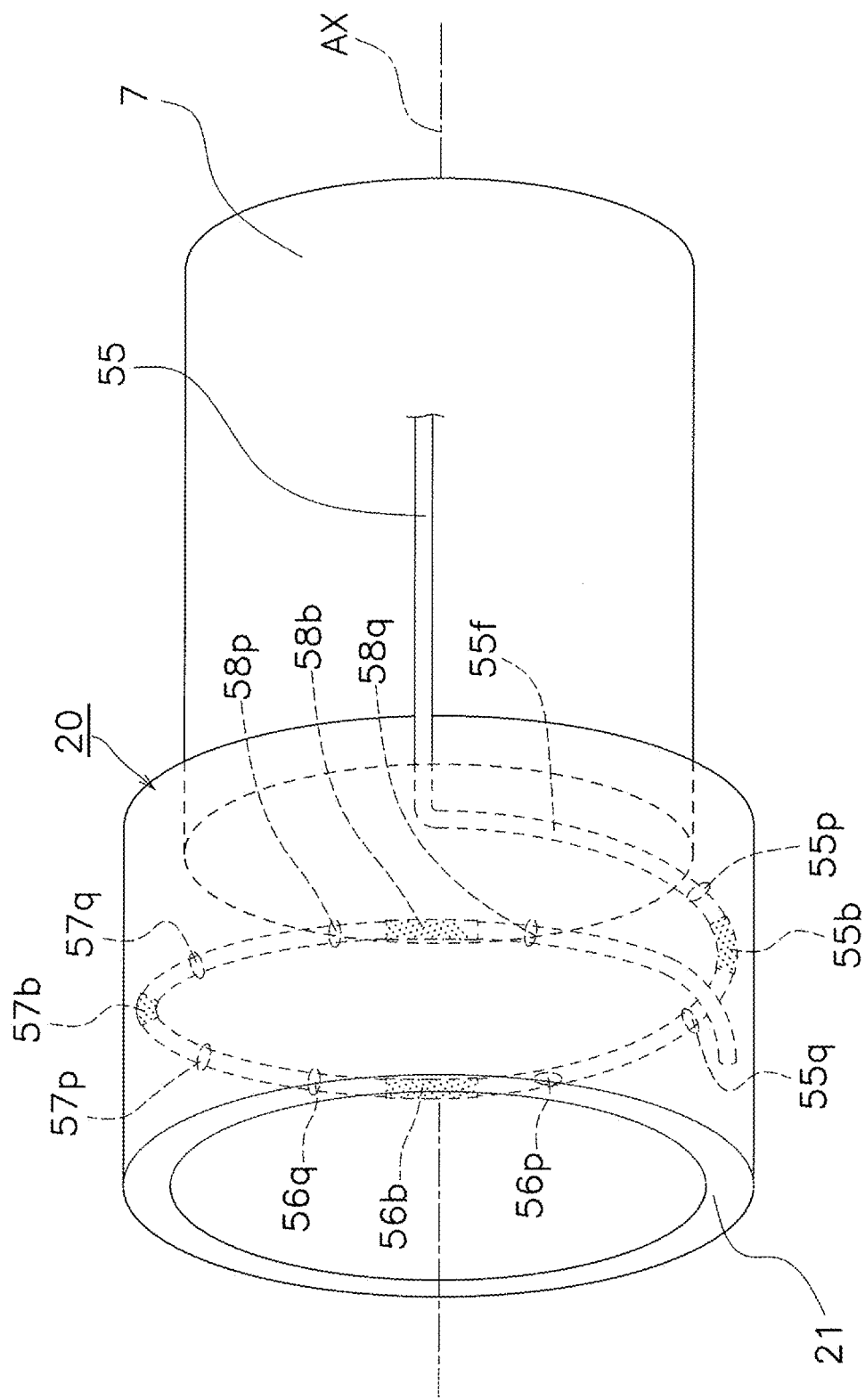
FIG. 12 is a perspective view illustrating one example of a sensor-equipped hood of Modification A.

FIG. 12 illustrates the sensor-equipped hood 20 in which one FBG sensor 55 is arranged. The FBG sensor 55 and the hood main body 21 form the sensor-equipped hood 20. The FBG sensor 55 is transparent and has water resistance. Since the FBG sensor 55 is very thin and transparent, the influence of the FBG sensor 55 is extremely small in a case where the portion 100 of the human body is observed through the hood main body 21. The material of the FBG sensor 55 and the dimensions of each portion thereof can be the same as those of the FBG sensors 51 to 54. Part of an optical fiber 55f of the FBG sensor 55 is inserted into the hood main body 21. The optical fiber 55f extends spirally about the axis AX in the hood main body 21. Four Bragg gratings 55b, 56b, 57b, 58b of the FBG sensor 55 are arranged in the hood main body 21.

The optical fiber 55f is fixed to the hood main body 21 at first fixing points 55p, 56p, 57p, 58p in front of the Bragg gratings 55b, 56b, 57b, 58b and second fixing points 55q, 56q, 57q, 58q in back of the Bragg gratings 55b, 56b, 57b, 58b. The optical fiber 55f may be fixed at the first fixing points 55p, 56p, 57p, 58p and the second fixing points 55q, 56q, 57q, 58q such that the optical fiber 55f and the hood main body 21 are joined to each other so as not to be separated in a linear region. A method of fixing the optical fiber 55f may be a physical fixing method such as screwing, fitting, clamping, taping, wedging, or caulking, or may be a chemical fixing method such as an adhesive.

In the FBG sensor 55, the wavelength of reflected light at each of the Bragg gratings 55b, 56b, 57b, 58b changes based on fluctuation of the first fixing points 55p, 56p, 57p, 58p in the hood main body 21. Based on such a change in the wavelength, the force applied to the hood main body 21 can be measured.

In the FBG sensor 55 illustrated in FIG. 12, the plurality of Bragg gratings 55b, 56b, 57b, 58b are arranged in one optical fiber 55f, and the plurality of first fixing points 55p, 56p, 57p, 58p are arranged corresponding to the Bragg gratings 55b, 56b, 57b, 58b. The FBG sensor 55 configured as described above can measure the stress at a plurality of locations in the hood main body 21 with one optical fiber 55f.

More specifically, when the compressive stress in the radial direction as illustrated in FIG. 10C is applied to the hood main body 21, an interval between the first fixing point 55p, 56p, 57p, 58p and the second fixing point 55q, 56q, 57q, 58q arranged at positions apart from each other in the circumferential direction decreases. When the interval between the first fixing point 55p, 56p, 57p, 58p and the second fixing point 55q, 56q, 57q, 58q decreases, the interval of the Bragg grating 55b, 56b, 57b, 58b also decreases, and the wavelength of the reflected light at the Bragg grating 55b, 56b, 57b, 58b changes.

When the tensile stress in the radial direction as illustrated in FIG. 10B is applied to the hood main body 21, the interval between the first fixing point 55p, 56p, 57p, 58p and the second fixing point 55q, 56q, 57q, 58q arranged at the positions apart from each other in the circumferential direction increases. When the interval between the first fixing point 55p, 56p, 57p, 58p and the second fixing point 55q, 56q, 57q, 58q increases, the interval of the Bragg grating 55b, 56b, 57b, 58b also increases, and the wavelength of the reflected light at the Bragg grating 55b, 56b, 57b, 58b changes.

In the above-described case, the first fixing point 55p, 56p, 57p, 58p can be taken as a fifth point, the second fixing point 55q, 56q, 57q, 58q can be taken as a sixth point, and the fifth point and the sixth point can be taken as being at positions apart from each other in the circumferential direction of the hood main body 21. In addition, the Bragg grating 55b, 56b, 57b, 58b can be taken as a third Bragg grating arranged between the fifth point and the sixth point.

(3-2) Modification B

In the above-described embodiment, as illustrated in FIG. 7, the case where the optical fibers 51f, 52f, 53f, 54f are arranged in parallel with the axis AX of the hood main body 21 in the hood main body 21 has been described. Moreover, in Modification A, as illustrated in FIG. 12, the case where the optical fiber 55f is spirally arranged in the hood main body 21 has been described. However, the sensor arrangement form is not limited to the sensor arrangement forms of the embodiment and Modification A.

Figure 13A:
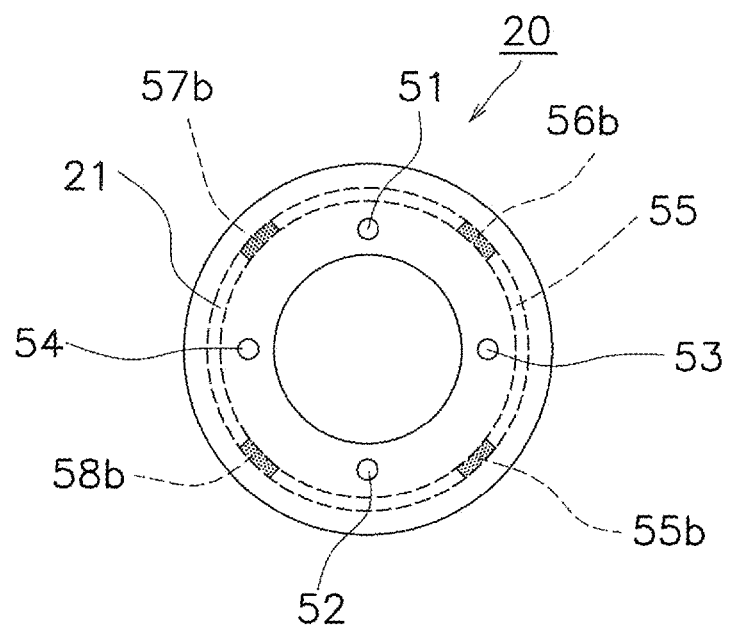
FIG. 13A is a front view illustrating one example of a sensor-equipped hood of Modification B.
Figure 13B:
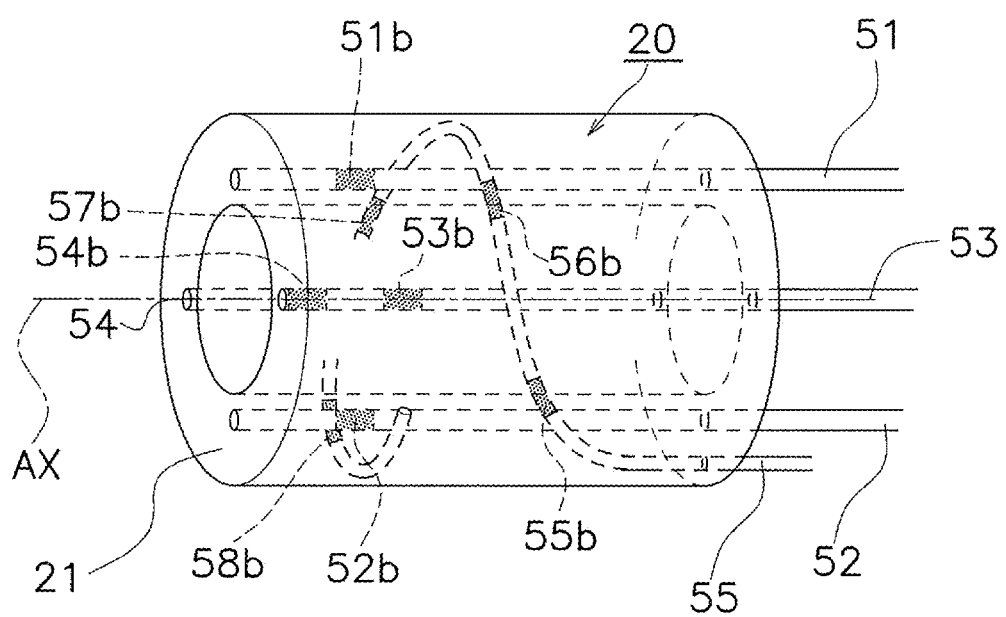
FIG. 13B is a perspective view illustrating one example of the sensor-equipped hood of Modification B.

FIGS. 13A, 13B, 14A, 14B, 15A, and 15B illustrate other sensor arrangement forms. In FIGS. 13A, 13B, 14A, 14B, 15A, and 15B, the first fixing point and the second fixing point are omitted. For example, the FBG sensors 51, 52, 53, 54, 55 illustrated in FIGS. 13A and 13B are fixed at fixing points similar to the first fixing points 51p, 52p, 53p, 54p, 55p and the second fixing points 51q, 52q, 53q, 54q, 55q illustrated in FIGS. 7 and 12.

FIGS. 13A and 13B illustrate the sensor-equipped hood 20 in which the FBG sensors 51, 52, 53, 54, 55 described in the above-described embodiment and Modification A are combined in one hood main body 21. FIG. 13A illustrates the sensor-equipped hood 20 as viewed from the tip end side along the axial direction, and FIG. 13B illustrates the sensor-equipped hood 20 viewed obliquely. The sensor-equipped hood 20 illustrated in FIGS. 13A and 13B can measure the stress described in the above-described embodiment and Modification A.

Figure 14A:
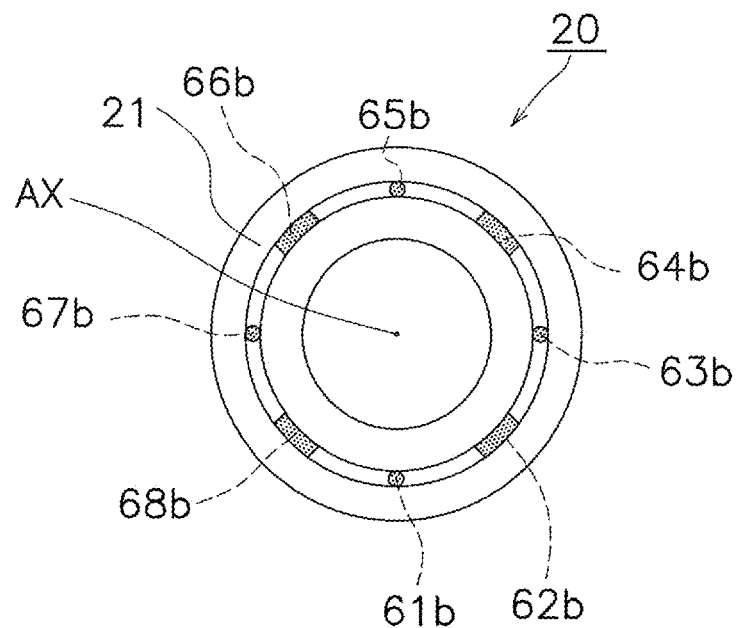
FIG. 14A is a front view illustrating another example of the sensor-equipped hood of Modification B.
Figure 14B:
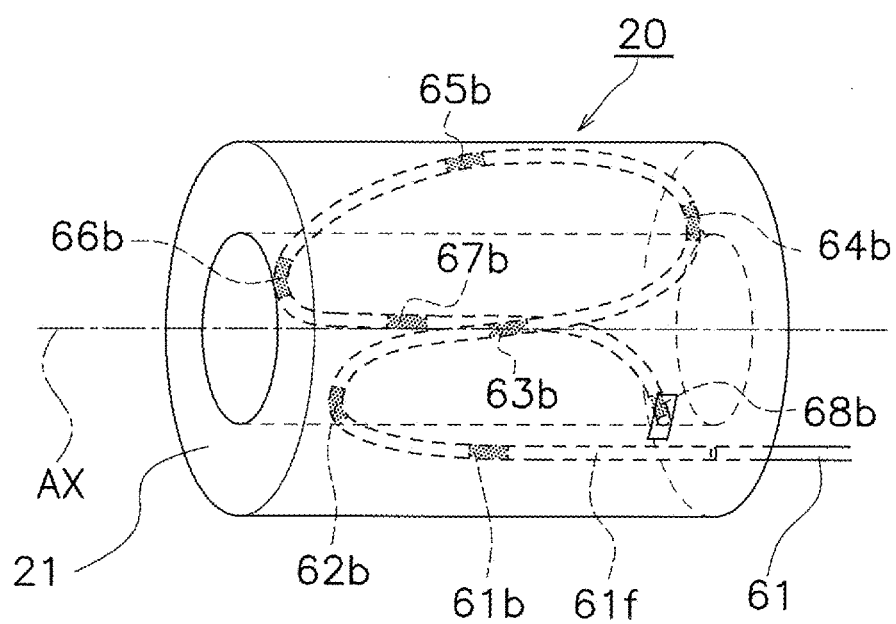
FIG. 14B is a perspective view illustrating another example of the sensor-equipped hood of Modification B.

In an FBG sensor 61 illustrated in FIGS. 14A and 14B, eight Bragg gratings 61b, 62b, 63b, 64b, 65b, 66b, 67b, 68b are formed in one optical fiber 61f. The optical fiber 61f is three-dimensionally arranged in the hood main body 21. With this configuration, the Bragg gratings 61b, 63b, 65b, 67b can measure stress in the direction along the axis AX. As illustrated in FIG. 14A, the Bragg gratings 63b, 65b, 67b are arranged at positions rotated by 45 degrees, 90 degrees, and 135 degrees about the axis AX with reference to the Bragg grating 61b. Thus, the Bragg gratings 61b, 65b, 63b, 67b illustrated in FIG. 14A can measure stress similar to that measured by the Bragg gratings 51b, 52b, 53b, 54b of the embodiment. Moreover, as illustrated in FIG. 14A, the Bragg gratings 64b, 66b, 68b are arranged at positions rotated by 45 degrees, 90 degrees, and 135 degrees about the axis AX with reference to the Bragg grating 62b. Using the Bragg gratings 62b, 64b, 66b, 68b illustrated in FIG. 14A, the tensile stress and the compressive stress in the radial direction of the hood main body 21 can be measured as in the Bragg gratings 55b, 56b, 57b, 58b of the embodiment.

Figure 15A:
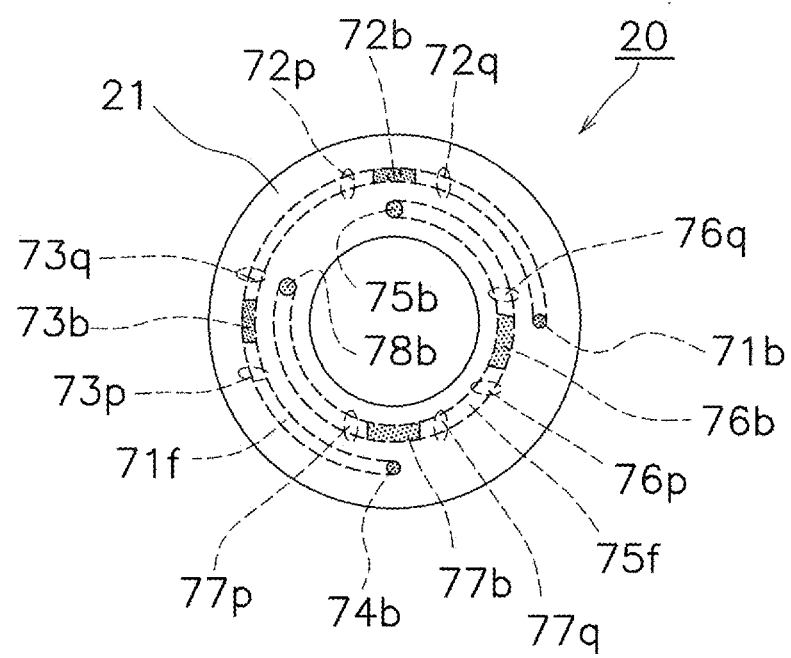
FIG. 15A is a front view illustrating another example of the sensor-equipped hood of Modification B.
Figure 15B:
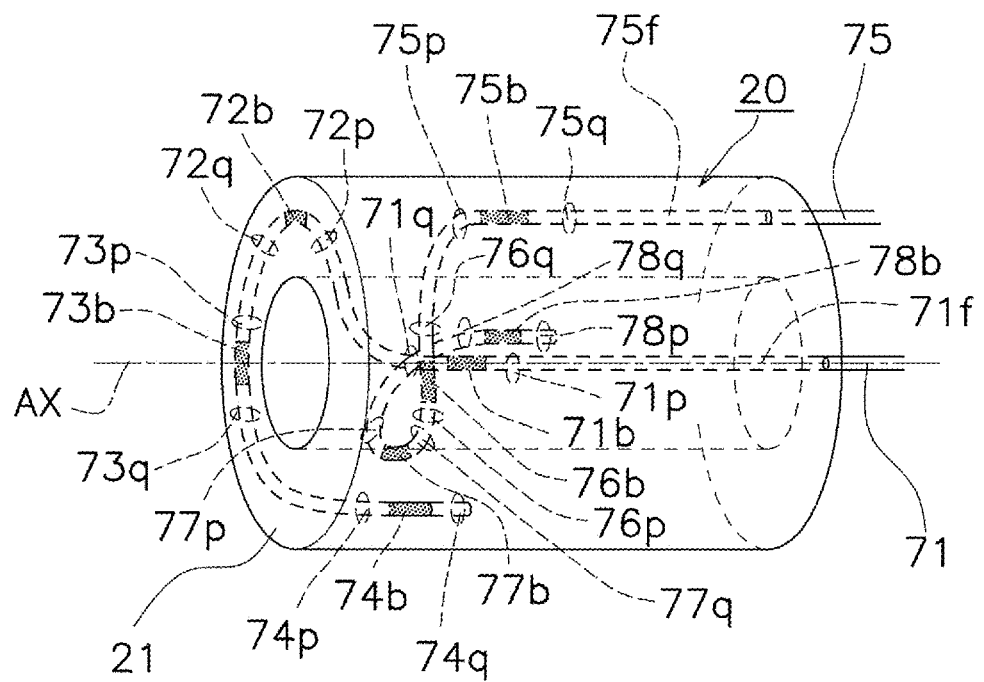
FIG. 15B is a perspective view illustrating another example of the sensor-equipped hood of Modification B.

Optical fibers 71f, 75f of FBG sensors 71, 75 illustrated in FIGS. 15A and 15B have a portion along the axis AX and a portion rotating about the axis AX in the hood main body 21. The FBG sensor 71 has Bragg gratings 71b, 72b, 73b, 74b. A first fixing point 71p, 72p, 73p, 74p and a second fixing point 71q, 72q, 73q, 74q are arranged on both sides of the Bragg grating 71b, 72b, 73b, 74b. The FBG sensor 75 has Bragg gratings 75b, 76b, 77b, 78b. A first fixing point 75p, 76p, 77p, 78p and a second fixing point 75q, 76q, 77q, 78q are arranged on both sides of the Bragg grating 75b, 76b, 77b, 78b. The tensile stress and the compressive stress in the axial direction can be measured by the Bragg gratings 71b, 78b, 74b, 75b extending in the direction along the axis AX, similarly to the Bragg gratings 51b, 52b, 53b, 54b illustrated in FIGS. 13A and 13B. In addition, the Bragg gratings 72b, 73b, 77b, 76b extending in the circumferential direction about the axis AX can measure the compressive stress and the tensile stress in the radial direction as illustrated in FIGS. 10A and 10B, similarly to the Bragg gratings 55b, 56b, 57b, 58b illustrated in FIGS. 13A and 13B. Further, since the direction in which the optical fiber 71f is wound and the direction in which the optical fiber 75f is wound are opposite to each other, the twisting stress can be detected and measured. In FIG. 15A, in a case where the tip end of the hood main body 21 is twisted clockwise, the compressive stress is applied to the Bragg gratings 73b, 72b, and the tensile stress is applied to the Bragg gratings 75b, 77b. Conversely, in FIG. 15A, in a case where the tip end of the hood main body 21 is twisted counterclockwise, the tensile stress is applied to the Bragg gratings 73b, 72b, and the compressive stress is applied to the Bragg gratings 75b, 77b. On the other hand, for example, when the compressive stress in the radial direction as illustrated in FIG. 10A is applied, the compressive stress is applied not only to the Bragg gratings 73b, 72b but also to the Bragg gratings 75b, 77b.

(3-3) Modification C

Figure 16A:
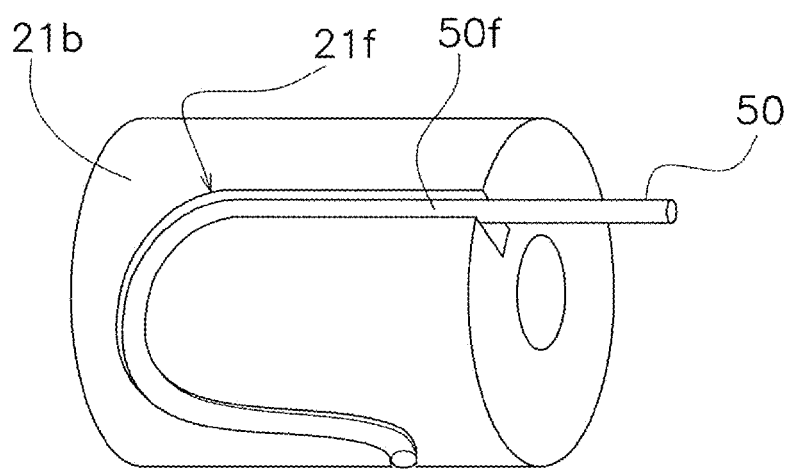
FIG. 16A is a perspective view of an inner tube for describing a method of fixing an FBG sensor in Modification C.
Figure 16B:
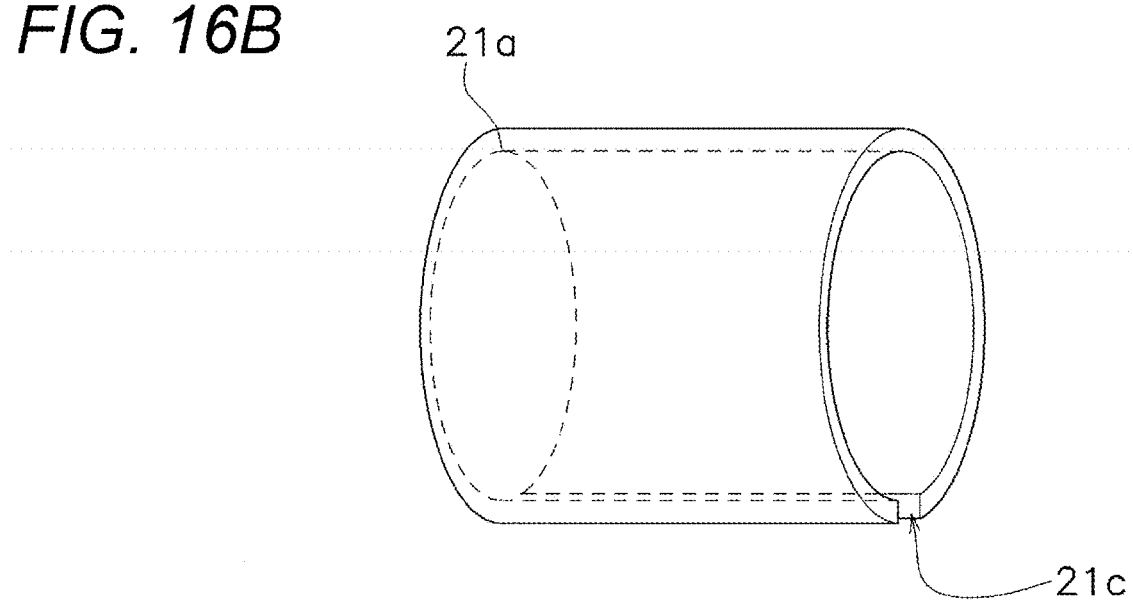
FIG. 16B is a perspective view of an outer tube for describing the method of fixing the FBG sensor in Modification C.
Figure 16C:
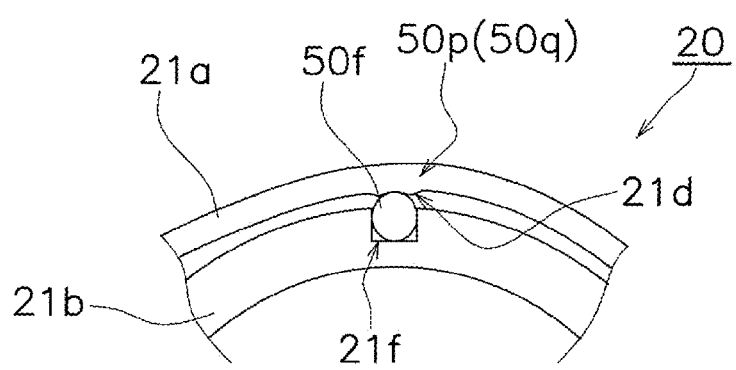
FIG. 16C is an enlarged sectional view partially illustrating the outer tube, the inner tube, and the FBG sensor for describing the method of fixing the FBG sensor in Modification C.

In the above-described embodiment, the case where the optical fiber 51f is installed straight in parallel with the axis AX in the hood main body 21 has been described with reference to FIGS. 9A and 9B. However, as illustrated in FIGS. 16A, 16B, and 16C, the groove 21f may be formed in a U shape.

Moreover, for the fixing method, force for elastically deforming the outer tube 21a may be used. In this case, a slit 21c is formed in the outer tube 21a. The outer tube 21a cut at the slit 21c is expanded and covers the inner tube 21b. An optical fiber 50f is fixed by force of the expanded outer tube 21a returning to an original diameter. In this case, a protrusion 21d may be provided on the inner peripheral surface of the outer tube 21a. A location where the protrusion 21d is provided is a first fixing point 50p or a second fixing point 50q.

Instead of providing the slit 21c, the outer tube 21a provided with no slit 21c may be expanded by thermal expansion, or the inner tube 21b may be cooled and contracted. In this manner, the inner tube 21b may be fitted in the outer tube 21a.

Alternatively, a heat shrinkable tube may be used as the outer tube 21a. When the heat shrinkable tube is used as the outer tube 21a, the optical fiber 50f may be configured to protrude from the surface of the inner tube 21b by making a location corresponding to the first fixing point 50p or the second fixing point 50q shallow in the groove 21f of the inner tube 21b, instead of providing the protrusion on the outer tube 21a.

(3-4) Modification D

Figure 17A:
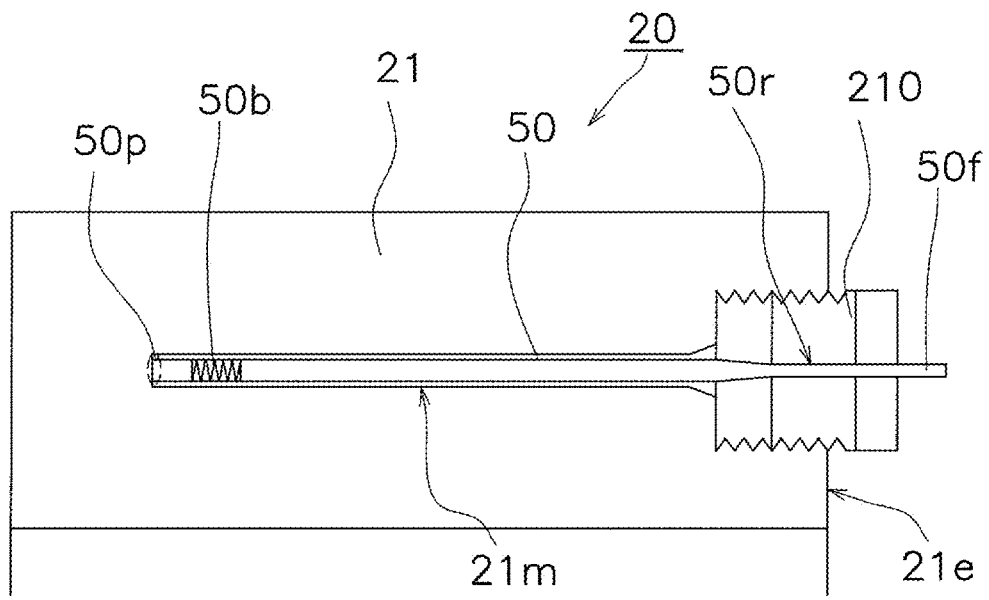
FIG. 17A is a schematic sectional view for describing one example of a method of fixing an FBG sensor in Modification D.

In the above-described embodiment, for example, the case where two fixing points such as the first fixing point 51p and the second fixing point 51q are present in the hood main body 21 has been described regarding the FBG sensor 51. However, one fixing point may be provided outside the hood main body 21. For example, in FIGS. 17A and 17B, a point other than the first fixing point 50p is fixed to a location other than the hood main body 21. Note that the location where such a point is fixed is a location where a position is fixed with respect to the hood main body 21. In FIG. 17A, a fixing point 50r paired with a first fixing point 50p of an FBG sensor 50 inserted into a hole 21m is fixed to a tapered screw 210. A Bragg grating 50b is arranged between the first fixing point 50p and the fixing point 50r. The tapered screw 210 is fixed to an end portion 21e of the hood main body 21. In the FBG sensor 50, the fixing point 50r is shrink-fitted in the tapered screw 210. The tapered screw 210 is fixed to the end portion 21e of the hood main body 21 with, for example, an adhesive. The FBG sensor 50, the hood main body 21, and the tapered screw 210 form the sensor-equipped hood 20.

Figure 17B:
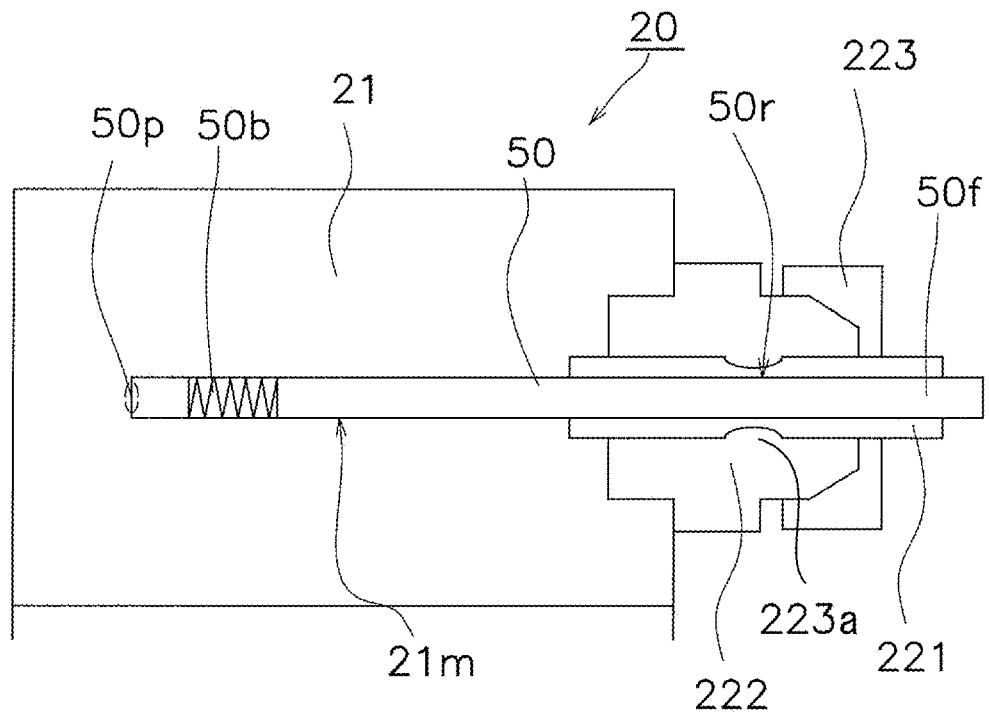
FIG. 17B is a schematic sectional view for describing another example of the method of fixing the FBG sensor in Modification D.

FIG. 17B illustrates another method of fixing the FBG sensor 50 to the end portion 21e of the hood main body 21. The optical fiber 50f inserted into the hole 21m of the hood main body 21 passes through a resin pipe 221. The inner diameter of the resin pipe 221 is equal to the outer diameter of the optical fiber 50f. The resin pipe 221 passes through a tapered ring 222. By tightening the tapered ring 222 with a nut 223, the inner diameter of the tapered ring 222 decreases. The nut 223 is a through-type resin joint. A protrusion 223a is formed on the inner peripheral surface of the tapered ring 222. Pressure is applied from the protrusion 223a to the optical fiber 50f through the resin pipe 221, and the optical fiber 50f is fixed to the tapered ring 222 accordingly. The tapered ring 222 is fixed to the end portion 21e of the hood main body 21. The tapered ring 222 is fixed to the end portion 21e of the hood main body 21 with, for example, an adhesive. The FBG sensor 50, the hood main body 21, the resin pipe 221, the tapered ring 222, and the nut 223 form the sensor-equipped hood 20.

(3-5) Modification E

Figure 18A:
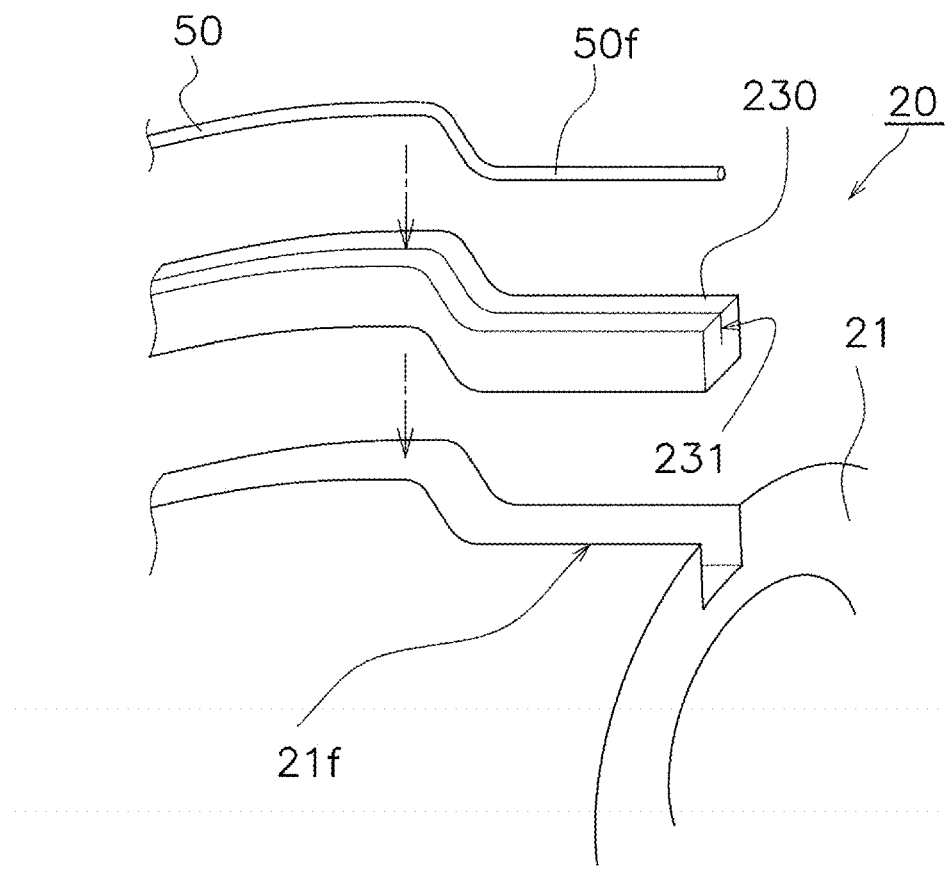
FIG. 18A is a schematic exploded perspective view for describing one example of a method of fixing an FBG sensor in Modification E.
Figure 18B:
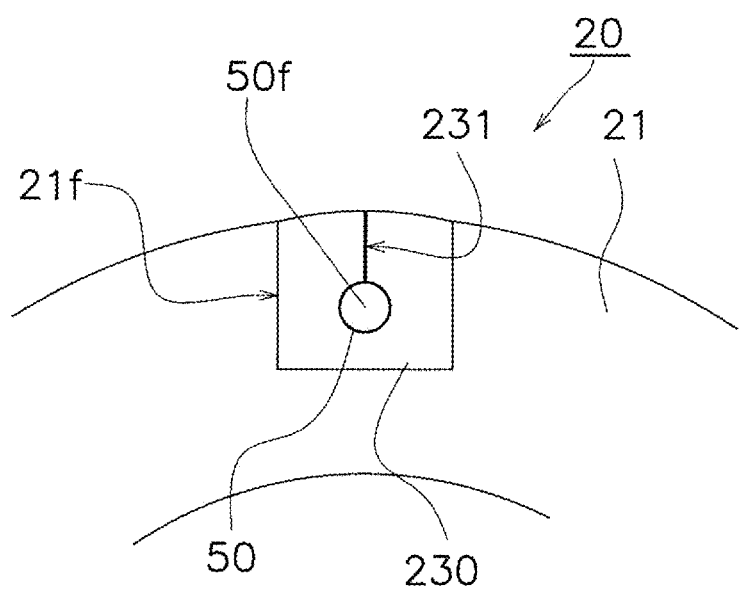
FIG. 18B is a schematic partially enlarged sectional view for describing one example of the method of fixing the FBG sensor in Modification E.

FIGS. 18A and 18B illustrate another method of fixing the FBG sensor 50. The groove 21f is formed in the surface of the hood main body 21. A rubber 230 having a portion slightly larger than the groove 21f is prepared in accordance with the shape of the groove 21f. The rubber 230 has a slit 231. The slit 231 is cut so as to be arranged along the groove 21f when the rubber 230 is fitted in the groove 21f. When the rubber 230 is fitted in the groove 21f, the rubber 230 is compressed by the hood main body 21, and the optical fiber 51f is fixed to the hood main body 21. In this case, the shape of the rubber 230 is set such that the rubber 230 is compressed at portions corresponding to the first fixing point and the second fixing point. For example, the groove 21f is formed with the same width over the entirety thereof. The rubber 230 is also formed to have the same width as the width of the groove 21f, except for portions corresponding to the first fixing point and the second fixing point, and is formed such that the widths of the portions corresponding to the first fixing point and the second fixing point are larger than the width of the groove 21f.

Alternatively, instead of the rubber 230, the optical fiber 50f may be fixed with an adhesive at locations corresponding to the first fixing point and the second fixing point in the groove 21f. Alternatively, the optical fiber 50f may be installed in the groove 21f by using both the rubber 230 and the adhesive.

(3-6) Modification F

Figure 19A:
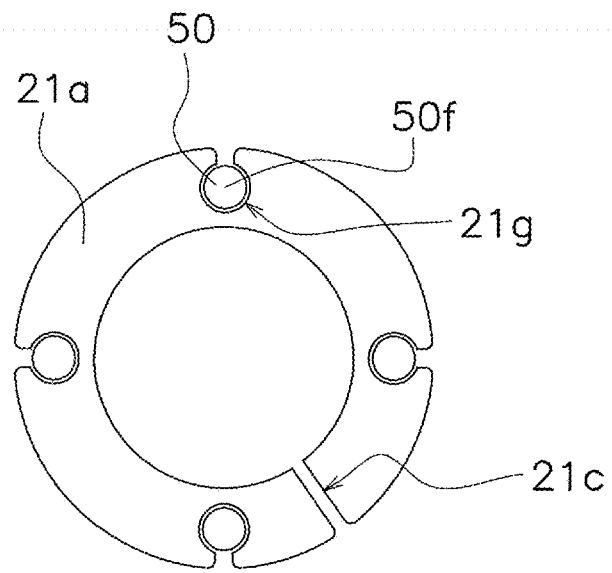
FIG. 19A is a schematic sectional view of an outer tube in which an optical fiber is fitted for describing one example of a method of fixing an FBG sensor in Modification F.
Figure 19B:
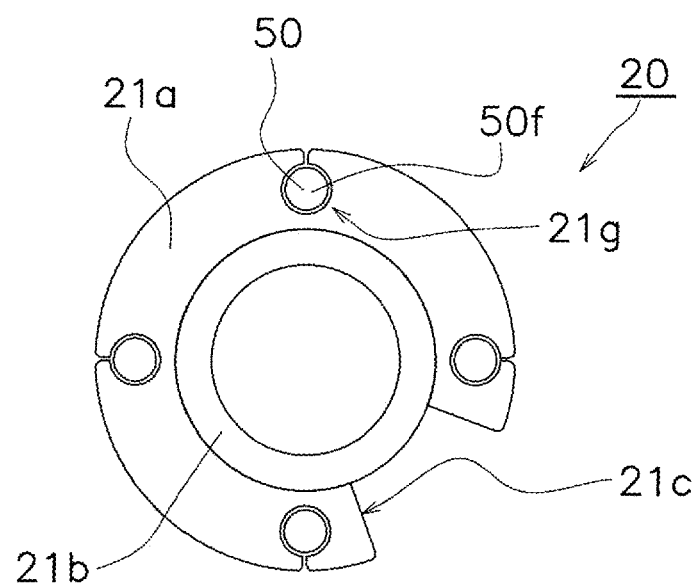
FIG. 19B is a schematic sectional view illustrating a state in which an inner tube is fitted in the outer tube for describing one example of the method of fixing the FBG sensor in Modification F.

FIGS. 19A and 19B illustrate another method of fixing the FBG sensor 50. The hood main body 21 includes the outer tube 21a and the inner tube 21b. A groove 21g in which the optical fiber 50f of the FBG sensor 50 is fitted is formed in the surface of the outer tube 21a. The hood main body 21 is partially separated into a C shape by the slit 21c extending in the axial direction of the hood main body 21. After the optical fiber 50f has been fitted in the groove 21g, the inner tube 21b having an outer shape larger than the inner diameter of the outer tube 21a is inserted into the outer tube 21a. At this time, the outer tube 21a is expanded by the inner tube 21b. The groove 21g of the outer tube 21a tends to contract when expanded. The optical fiber 50f is fixed to the hood main body 21 by force for contracting the groove 21g. For example, the groove 21g is narrow at locations corresponding to the first fixing point and the second fixing point. With such a structure of the groove 21g, the optical fiber 50f is fixed at the first fixing point and the second fixing point.

Figure 20A:
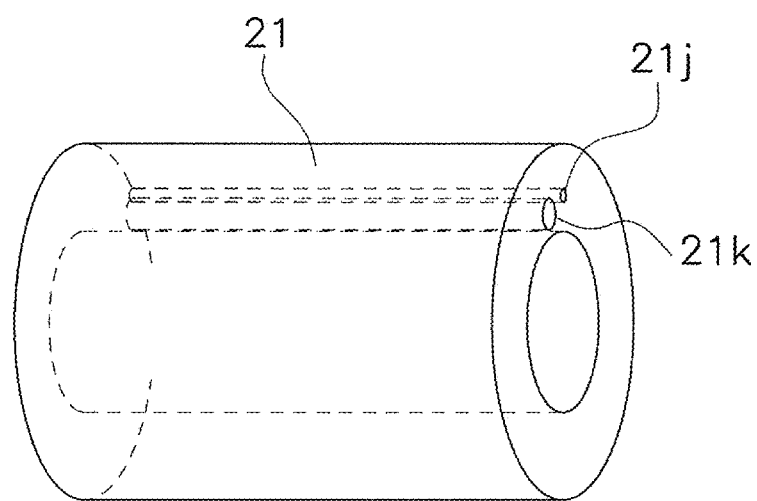
FIG. 20A is a perspective view of a hood main body for describing another example of the method of fixing the FBG sensor in Modification F.
Figure 20B:
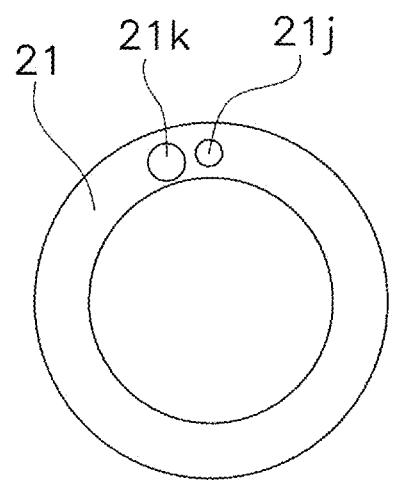
FIG. 20B is a front view of the hood main body for describing another example of the method of fixing the FBG sensor in Modification F.
Figure 20C:
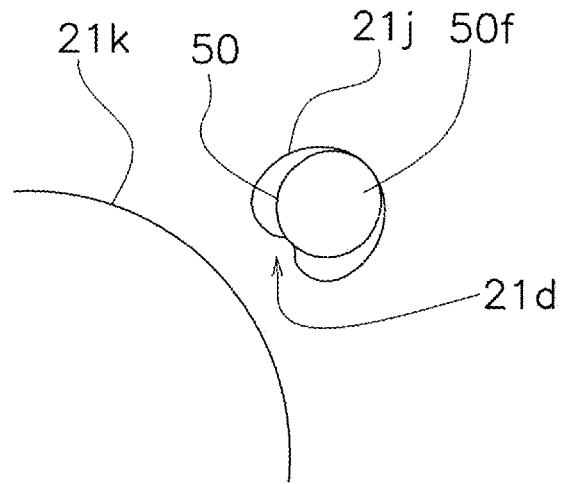
FIG. 20C is a schematic partially enlarged sectional view of the hood main body for describing another example of the method of fixing the FBG sensor in Modification F.

In FIGS. 19A and 19B, the outer tube 21a is deformed by the inner tube 21b to fix the FBG sensor 50, but the hood main body 21 may be deformed by a member other than the inner tube 21b to fix the FBG sensor 50. FIGS. 20A, 20B, and 20C illustrate another method of fixing the FBG sensor 50. In the hood main body 21, a through-hole 21k is formed in parallel with a through-hole 21j through which the optical fiber 50f passes. In a state in which the optical fiber 50f passes through the through-hole 21j, a round bar (not illustrated) having a diameter larger than the diameter of the through-hole 21k is inserted into the through-hole 21k. The round bar causes the periphery of the through-hole 21k to expand toward the through-hole 21j. For example, the protrusions 21d corresponding to the first fixing point and the second fixing point are provided in the through-hole 21j so that the optical fiber 50f can be fixed at the first fixing point and the second fixing point in the through-hole 21j by the protrusions 21d.

(3-7) Modification G

Figure 21:
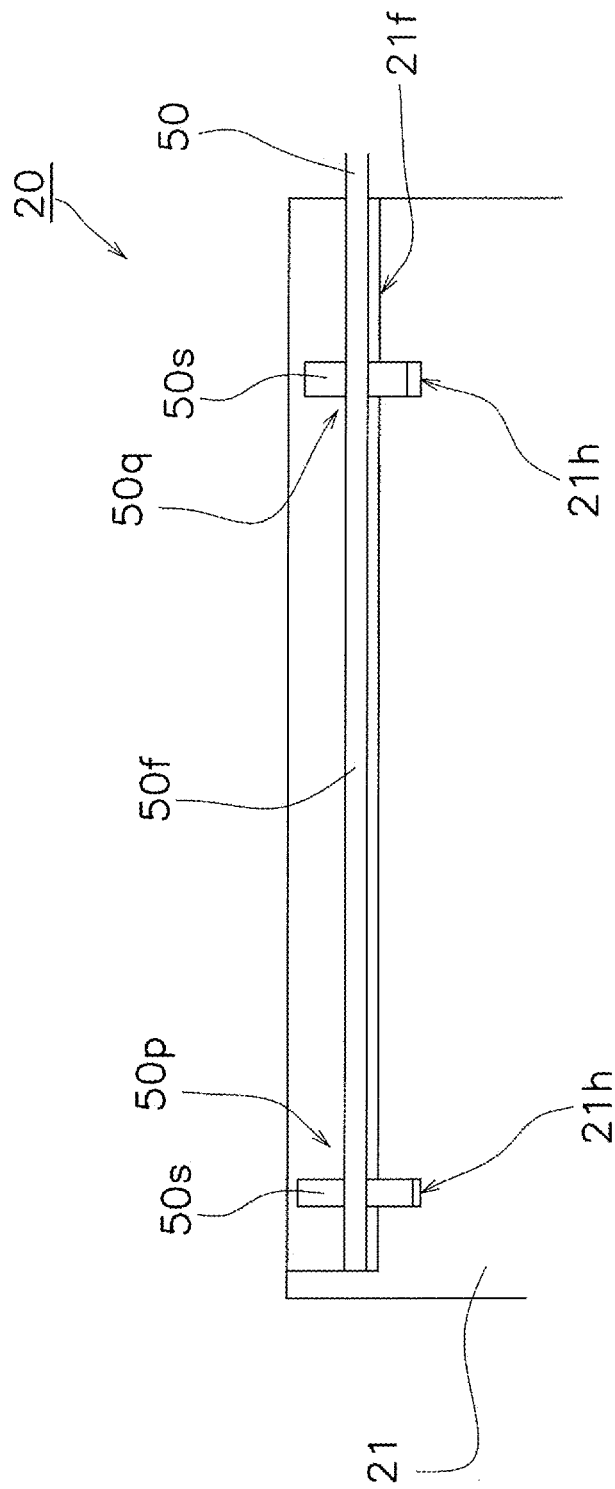
FIG. 21 is a schematic partially enlarged sectional view showing a hood main body and an FBG sensor for describing one example of a method of fixing an FBG sensor in Modification G.

FIG. 21 illustrates another method of fixing the FBG sensor 50. For example, a ring-shaped stopper 50s is attached to the optical fiber 50f of the FBG sensor 50. The position at which the stopper 50s is attached is a position corresponding to each of the first fixing point 50p and the second fixing point 50q. The stopper 50s is fixed to the optical fiber 50f by, for example, an adhesive or shrink fitting. The groove 21f in which the optical fiber 50f is fitted is formed in the surface of the hood main body 21. A hole 21h in which the stopper 50s is fitted is formed in the groove 21f. For example, the optical fiber 50f is fitted in the groove 21f, the stopper 50s is fitted in the hole 21h, and the groove 21f is filled with silicone rubber together with the optical fiber 50f. The FBG sensor 50 can measure the stress by a distance between the two holes 21h, which varies depending on the stress applied to the hood main body 21.

(3-8) Modification H

Figure 22A:
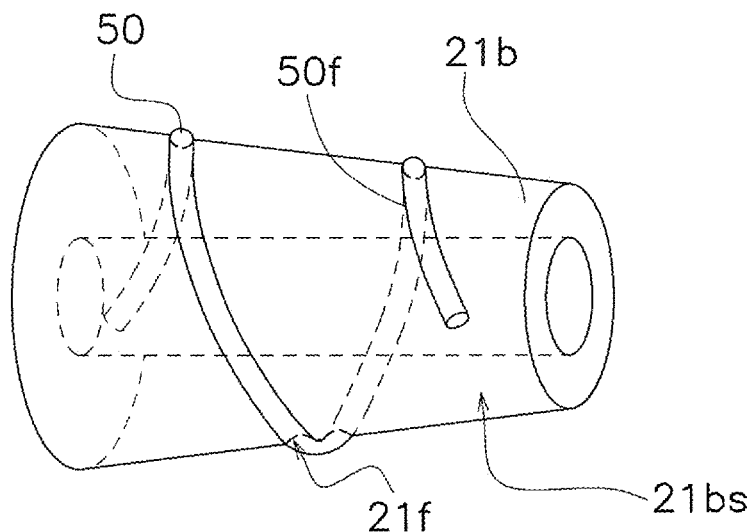
FIG. 22A is a schematic perspective view of an inner tube around which an FBG sensor is wound for describing one example of a method of fixing an FBG sensor in Modification H.
Figure 22B:
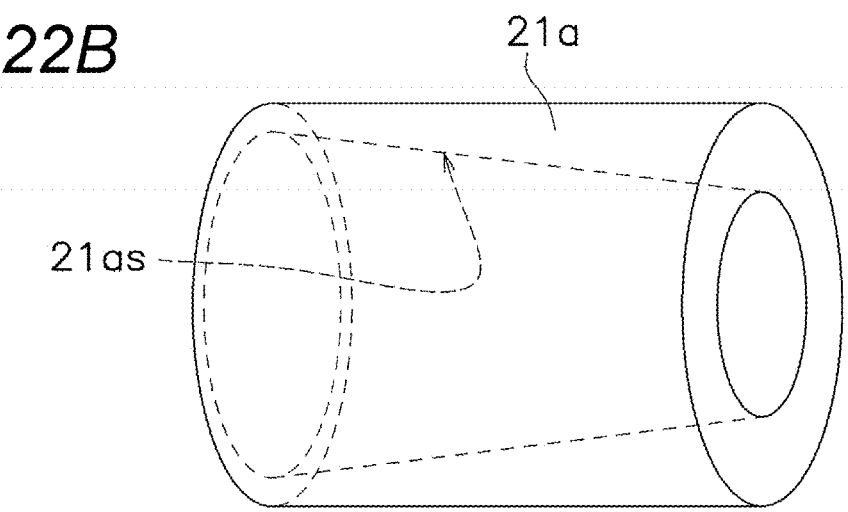
FIG. 22B is a schematic perspective view of an outer tube for describing one example of the method of fixing the FBG sensor in Modification H.
Figure 22C:
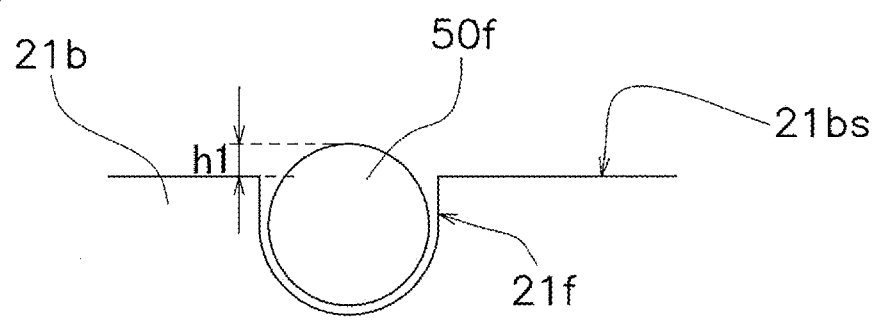
FIG. 22C is a schematic partially enlarged sectional view showing the FBG sensor and the inner tube for describing one example of the method of fixing the FBG sensor in Modification H.

FIGS. 22A, 22B, and 22C illustrate another method of fixing the FBG sensor 50. The inner tube 21b illustrated in FIG. 22A has a tapered outer surface 21bs. The groove 21f is formed in the outer surface 21bs of the inner tube 21b. In FIG. 22A, the groove 21f is formed spirally, but the shape of the groove 21f is not limited to the spiral shape. The outer tube 21a illustrated in FIG. 22B has a tapered inner surface 21as. As illustrated in FIG. 22C, locations corresponding to the first fixing point and the second fixing point in the groove 21f are slightly shallower than the diameter of the optical fiber 50f. Thus, at this location, the optical fiber 50f protrudes from the outer surface 21bs of the inner tube 21b by a slight height h1. The inner tube 21b around which the optical fiber 50f is wound is fitted in the outer tube 21a, and the outer surface 21bs of the inner tube 21b is pressed against the inner surface 21as of the outer tube 21a. In this manner, the optical fiber 50f is sandwiched and fixed between the inner tube 21b and the outer tube 21a at the locations corresponding to the first fixing point and the second fixing point.

(3-9) Modification I

Figure 23A:
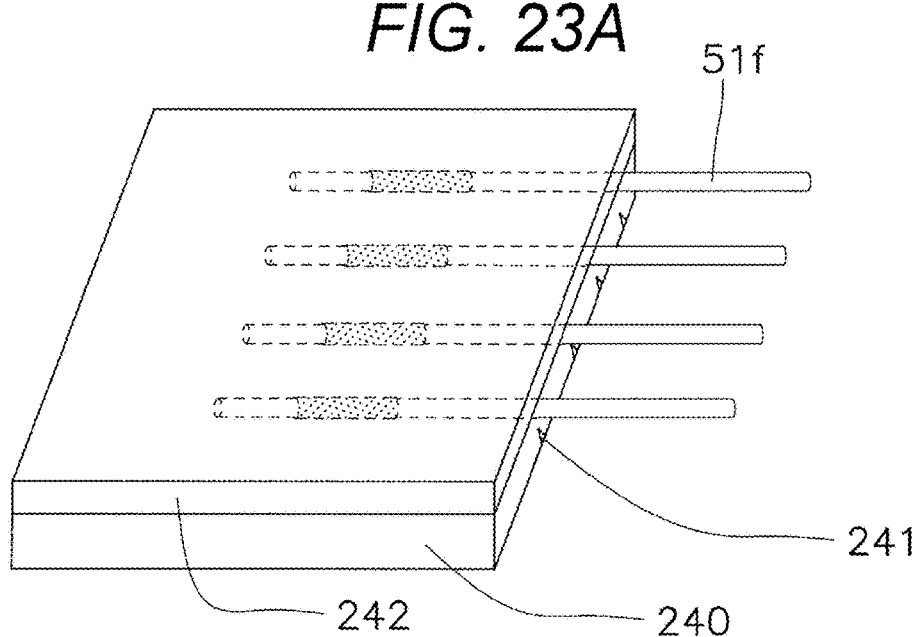
FIG. 23A is a schematic perspective view of a plate-shaped member to which an FBG sensor is fixed for describing one example of a method of fixing the FBG sensor in Modification I.
Figure 23B:
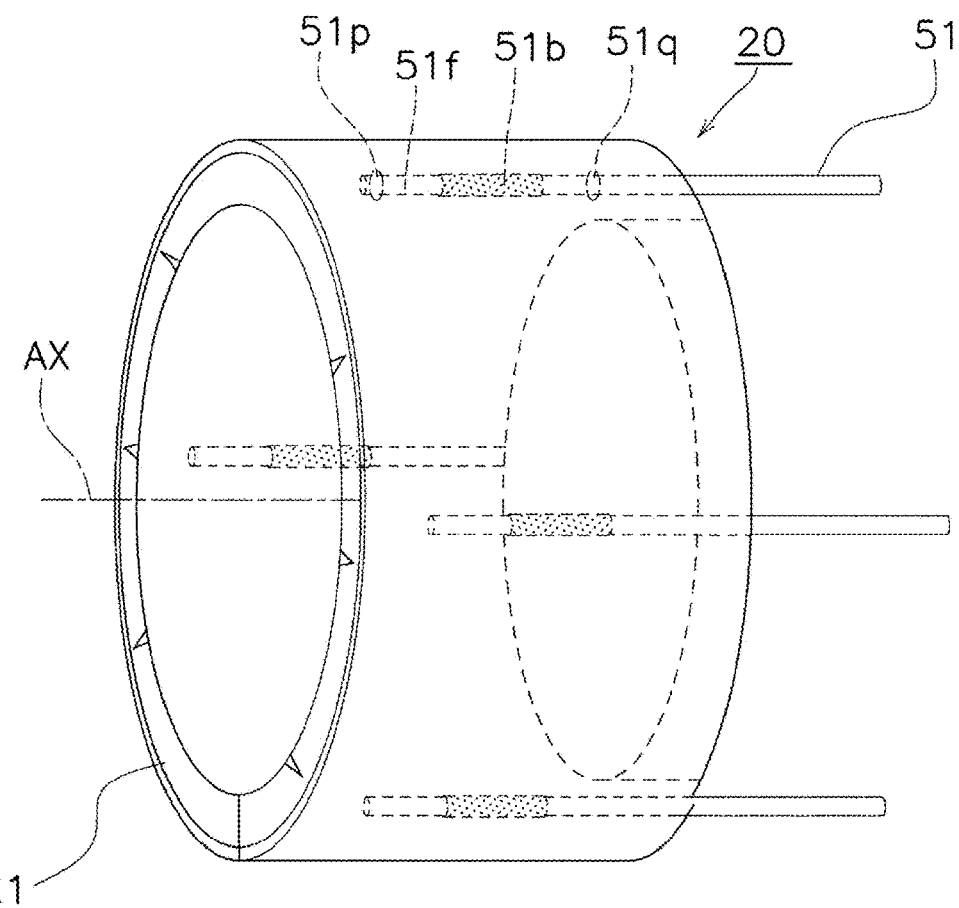
FIG. 23B is a schematic perspective view of a sensor-equipped hood formed by rounding the plate-shaped member of FIG. 23A.

FIGS. 23A and 23B illustrate another method of fixing the FBG sensor 50. A plurality of notches 241 are formed in a plate-shaped member 240 illustrated in FIG. 23. The notch 241 is formed linearly so as to extend along the axis AX of the hood main body 21 when formed in the hood main body 21. A coating layer 242 is formed on the optical fiber 50f with the optical fiber 50f fixed on the plate-shaped member 240. The plate-shaped member 240 is made of thermoplastic resin, and can be rounded by applying heat. Alternatively, the plate-shaped member 240 is formed of a member which is rounded by applying heat. By applying heat to the plate-shaped member 240 and rounding the plate-shaped member 240 into a tubular shape, the hood main body 21 as illustrated in FIG. 23B can be formed.

(3-10) Modification J

Figure 24A:
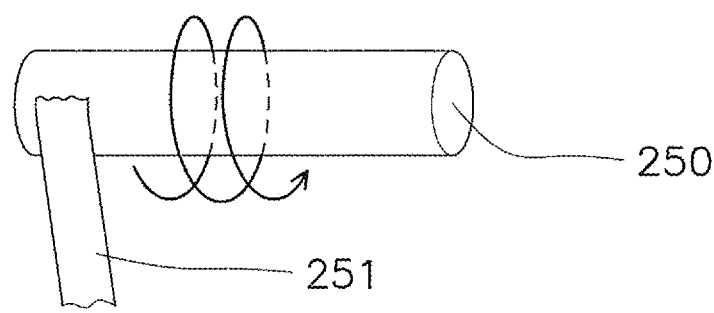
FIG. 24A is a schematic perspective view showing one example of a method of forming an inner tube in a method of fixing an FBG sensor in Modification J.

FIGS. 24A, 24B, 24C, and 24D illustrate another method of fixing the FBG sensor 50. In this fixing method, as illustrated in FIG. 24A, a tape-shaped member 251 is wound around a core 250. The tape-shaped member 251 is, for example, a resin tape. The tape-shaped member 251 is spirally wound around the core 250 as indicated by an arrow illustrated in FIG. 24A.

Figure 24B:
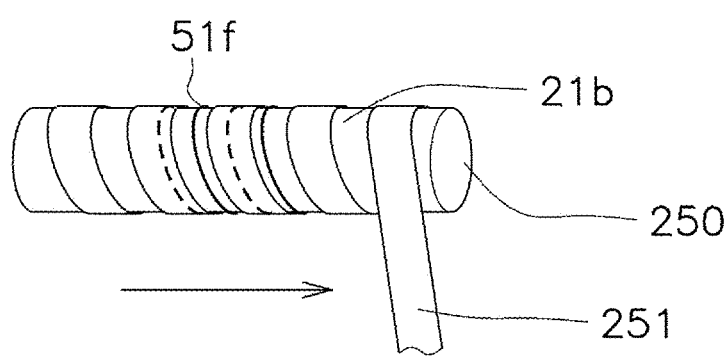
FIG. 24B is a schematic perspective view showing the state of winding of the FBG sensor around the inner tube in the method of fixing the FBG sensor in Modification J.

FIG. 24B illustrates a state in which the tape-shaped member 251 is wound around the entirety of the core 250 without a gap. The tape-shaped member 251 wound around the entirety of the core 250 forms the inner tube 21b. The optical fiber 50f is wound around and fixed to the inner tube 21b. For example, at locations corresponding to the first fixing point and the second fixing point, the optical fiber 50f is fixed to the inner tube 21b with an adhesive.

Figure 24C:
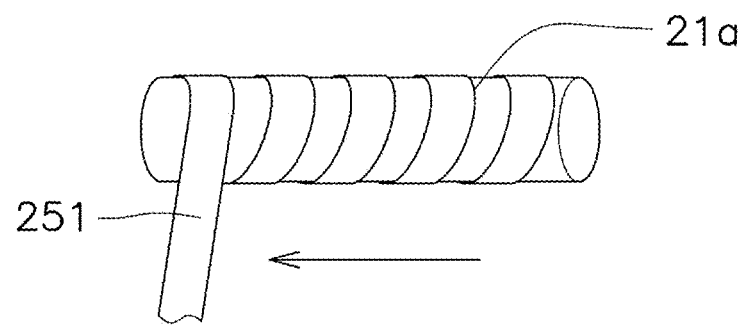
FIG. 24C is a schematic perspective view showing one example of a method of forming an outer tube in the method of fixing the FBG sensor in Modification J.

Next, as illustrated in FIG. 24C, the tape-shaped member 251 is further spirally wound around the inner tube 21b around which the optical fiber 50f has been wound, thereby forming the outer tube 21a.

Figure 24D:
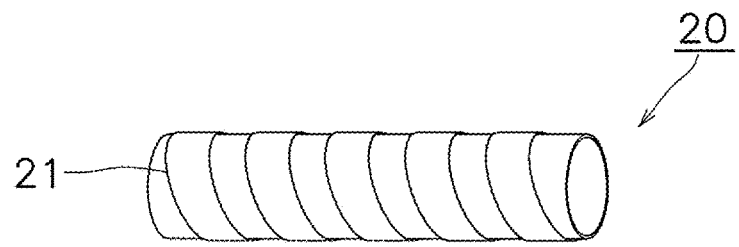
FIG. 24D is a schematic perspective view showing one example of a method of forming a sensor-equipped hood in the method of fixing the FBG sensor in Modification J.

The tape-shaped member 251 is cut in a state in which the outer tube 21a is formed, and the core 250 is removed. After the core 250 has been removed, formation of the hood main body 21 (as illustrated in FIG. 24D) having the optical fiber 50f therein is completed.

(3-11) Modification K

Figure 25A:
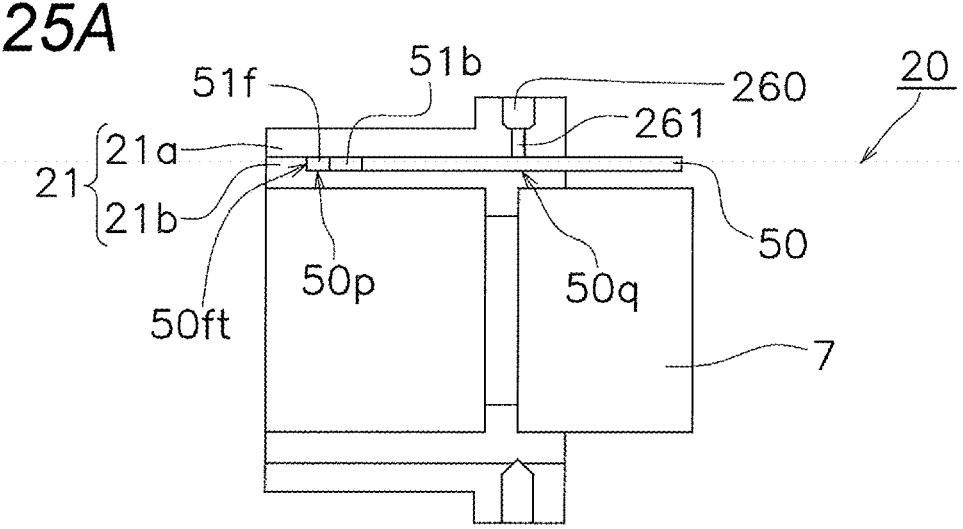
FIG. 25A is a schematic sectional view of a sensor-equipped hood to which an FBG sensor is attached for describing one example of a method of fixing the FBG sensor in Modification K.
Figure 25B:
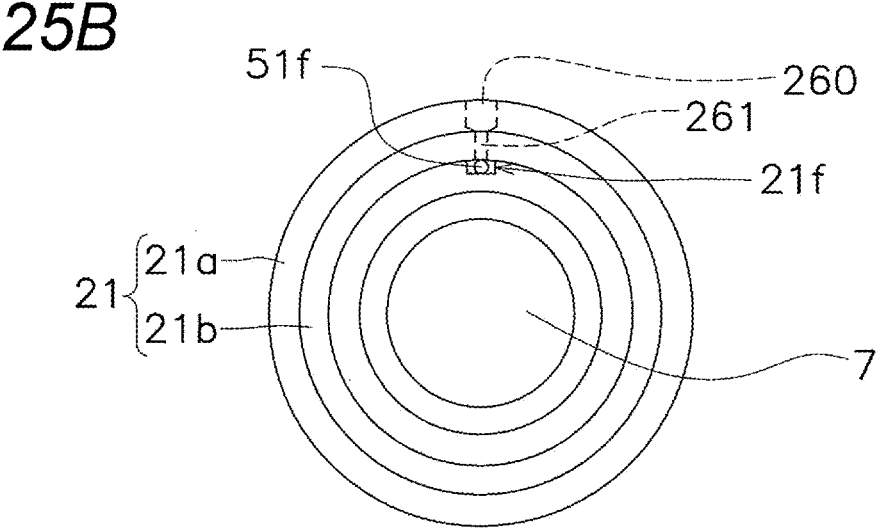
FIG. 25B is a schematic front view of the sensor-equipped hood for describing one example of the method of fixing the FBG sensor in Modification K.
Figure 25C:
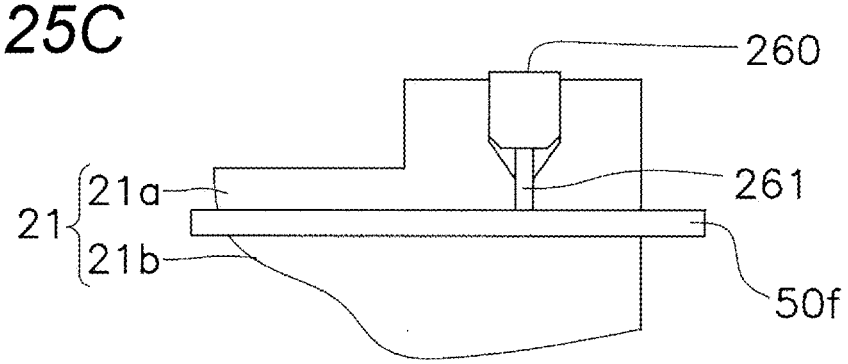
FIG. 25C is a schematic partially enlarged sectional view showing a fixing portion of the FBG sensor for describing one example of the method of fixing the FBG sensor in Modification K.

FIGS. 25A, 25B, and 25C illustrate another method of fixing the FBG sensor 50. FIG. 25A illustrates the section of the sensor-equipped hood 20, FIG. 25B illustrates the front of the sensor-equipped hood 20, and FIG. 25C illustrates a fixing location in closeup. The sensor-equipped hood 20 illustrated in FIGS. 25A to 25C includes the hood main body 21 including the outer tube 21a and the inner tube 21b. The optical fiber 50f is fitted in the groove 21f formed in the inner tube 21b. The outer tube 21a is formed with an internal thread for screwing a flat-ended set screw 260. A set piece 261 made of resin is arranged between the set screw 260 and the optical fiber 50f. By screwing the set screw 260 from the outer tube 21a, the set piece 261 is pressed by the set screw 260, and the optical fiber 50f can be fixed by the set piece 261. A location fixed by the set piece 261 is the second fixing point 50q. A tip end portion 50ft of the optical fiber 50f is fixed to the groove 21f with, for example, an adhesive. The portion fixed with the adhesive is the first fixing point 50p.

Figure 26A:
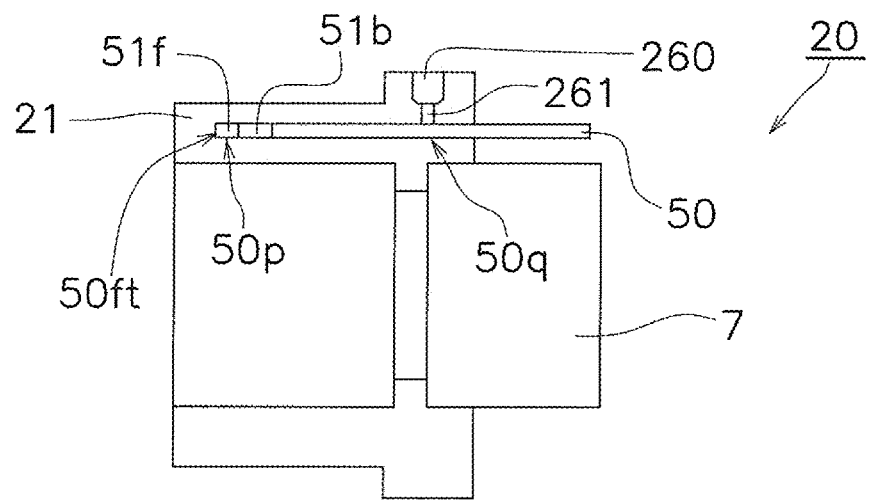
FIG. 26A is a schematic sectional view of the sensor-equipped hood to which the FBG sensor is attached for describing another example of the method of fixing the FBG sensor in Modification K.
Figure 26B:
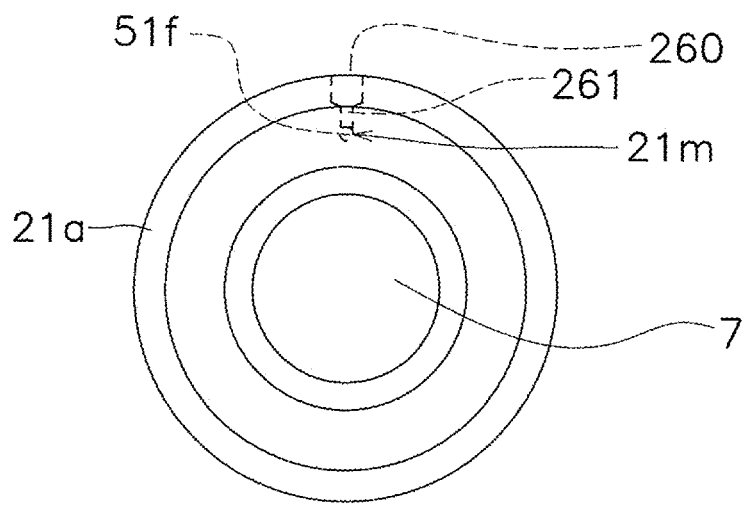
FIG. 26B is a schematic front view of the sensor-equipped hood for describing another example of the method of fixing the FBG sensor in Modification K.
Figure 26C:
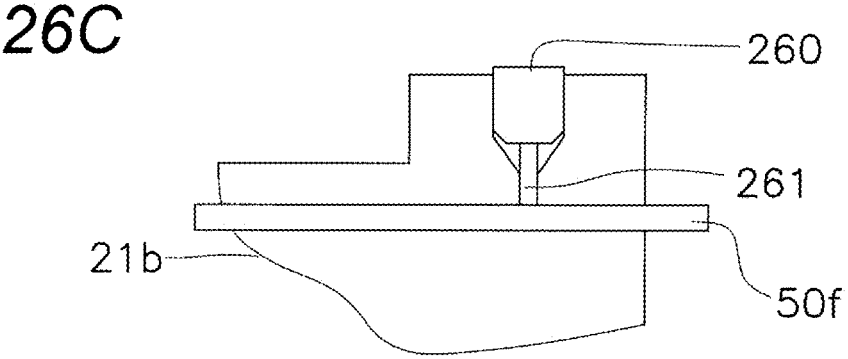
FIG. 26C is a schematic partially enlarged sectional view showing the fixing portion of the FBG sensor for describing another example of the method of fixing the FBG sensor in Modification K.

The method of fixing the FBG sensor 50 as illustrated in FIGS. 25A to 25C relates to fixing of the FBG sensor 50 to the hood main body 21 having the outer tube 21a and the inner tube 21b. In a similar manner, the FBG sensor 50 can be fixed to the hood main body 21 not divided into the outer tube 21a and the inner tube 21b. FIGS. 26A, 26B, and 26C illustrate fixing of the optical fiber 50f to the hood main body 21 not divided into the outer tube 21a and the inner tube 21b with the set screw 260. As illustrated in FIG. 26B, the optical fiber 50f is arranged in the hole 21m formed in the hood main body 21.

(3-12) Modification L

Figure 27A:
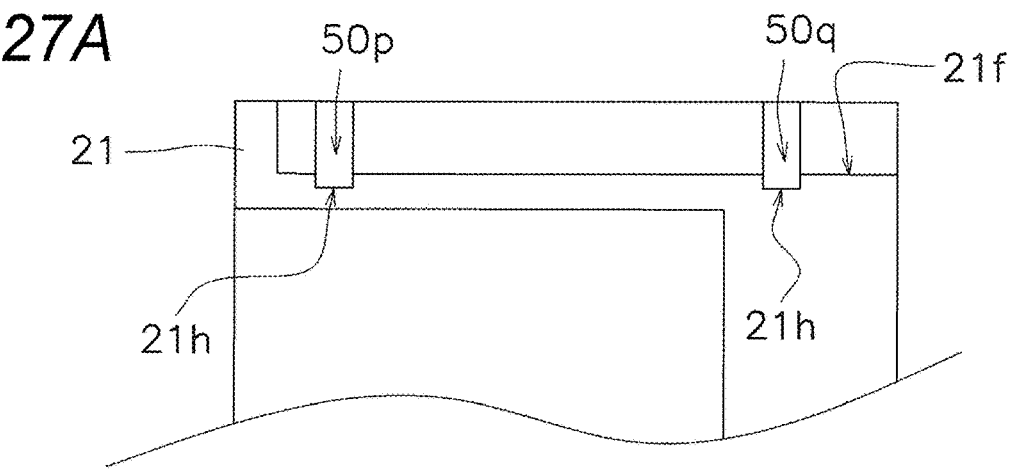
FIG. 27A is a schematic partially enlarged view of a hood main body for describing one example of a method of fixing an FBG sensor in Modification L.
Figure 27B:
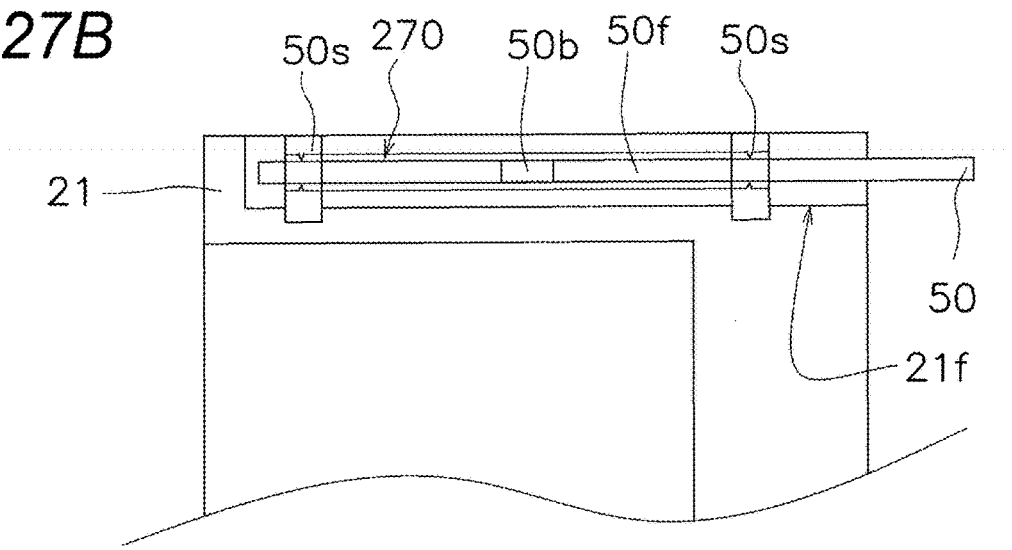
FIG. 27B is a schematic partially enlarged view illustrating a state in which the FBG sensor is attached to the hood main body of FIG. 27A.
Figure 27C:
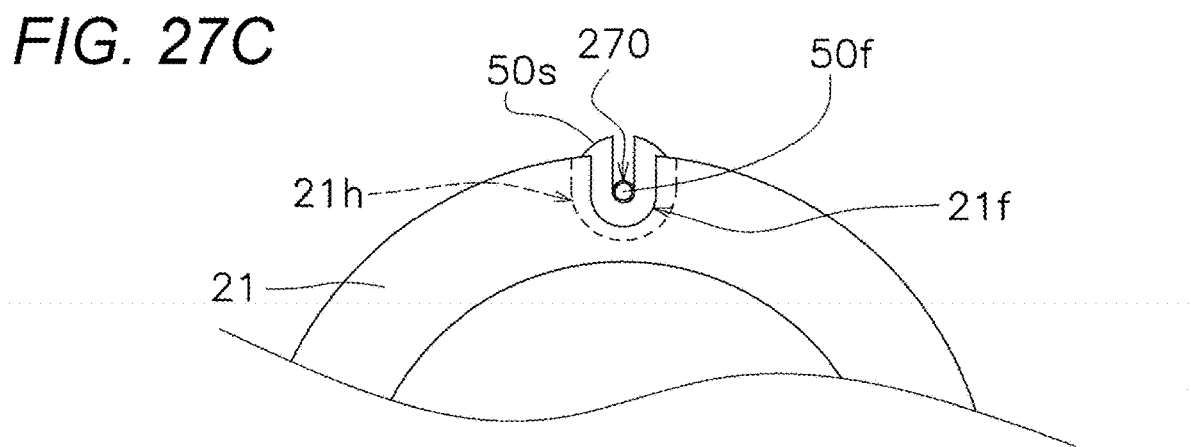
FIG. 27C is a schematic partial front view illustrating the state in which the FBG sensor is attached to the hood main body of FIG. 27A.

FIGS. 27A, 27B, and 27C illustrate another method of fixing the FBG sensor 50. For example, the ring-shaped stopper 50s is attached to the optical fiber 50f of the FBG sensor 50. The position at which the stopper 50s is attached is a position corresponding to each of the first fixing point 50p and the second fixing point 50q. The Bragg grating 50b is arranged between the first fixing point 50p and the second fixing point 50q. The stopper 50s is fixed to a protective tube 270 by, for example, an adhesive or shrink fitting. The optical fiber 50f passes through the protective tube 270. The protective tube 270 is a metal tube or a resin tube. Examples of the metal tube include a stainless steel tube. The optical fiber 50f is fixed by caulking, for example, at positions corresponding to the first fixing point 50p and the second fixing point 50q. The groove 21f in which the optical fiber 50f is fitted is formed in the surface of the hood main body 21. The hole 21h in which the stopper 50s is fitted is formed in the groove 21f.

For example, the protective tube 270 through which the optical fiber 50f passes is fitted in the groove 21f, the stopper 50s is fitted in the hole 21h, and the groove 21f is filled with silicone rubber together with the protective tube 270. The FBG sensor 50 changes the distance between the two holes 21h by the stress applied to the hood main body 21. The change in the distance between the holes 21h causes a change in the length of the protective tube 270 between the first fixing point 50p and the second fixing point 50q through the stoppers 50s. Since the optical fiber 50f is fixed to the protective tube 270, the stress is transmitted to the optical fiber 50f from the protective tube 270, and the FBG sensor 50 can measure the stress.

(3-13) Modification M

In Modification A described above, for example, the case where the plurality of Bragg gratings 55b, 56b, 57b, 58b are arranged in one optical fiber 55f has been described with reference to FIG. 12. For example, the case where the two first fixing points 55p, 56p and the two second fixing points 55q, 56q are provided for the Bragg gratings 55b, 56b has been described. However, the second fixing point 55q and the first fixing point 56p adjacent to each other may be integrated into one fixing point, and the Bragg gratings 55b, 56b may share such a fixing point. In this case, the first fixing point 55p, the Bragg grating 55b, the one fixing point (integrated point of the second fixing point 55q and the first fixing point 56p), the Bragg grating 56b, and the second fixing point 56q are arranged in this order.

(3-14) Modification N

In the above-described embodiment, the case where the stress is measured by the FBG sensors 50 to 55, 61, 71, 75 has been described. Using the FBG sensor with the Bragg grating for the sensor-equipped hood 20, the temperature of the hood main body 21 or the temperature around the hood main body 21 may be measured. In a case where the FBG sensor arranged in the hood main body 21 is used for measuring the temperature, the FBG sensor may be fixed to the hood main body 21 with, for example, the optical fiber passing through a silicone rubber or a metal tube softer than the hood main body 21 such that the stress from the hood main body 21 is not applied to the FBG sensor.

(4) Experimental Example

Figure 28:
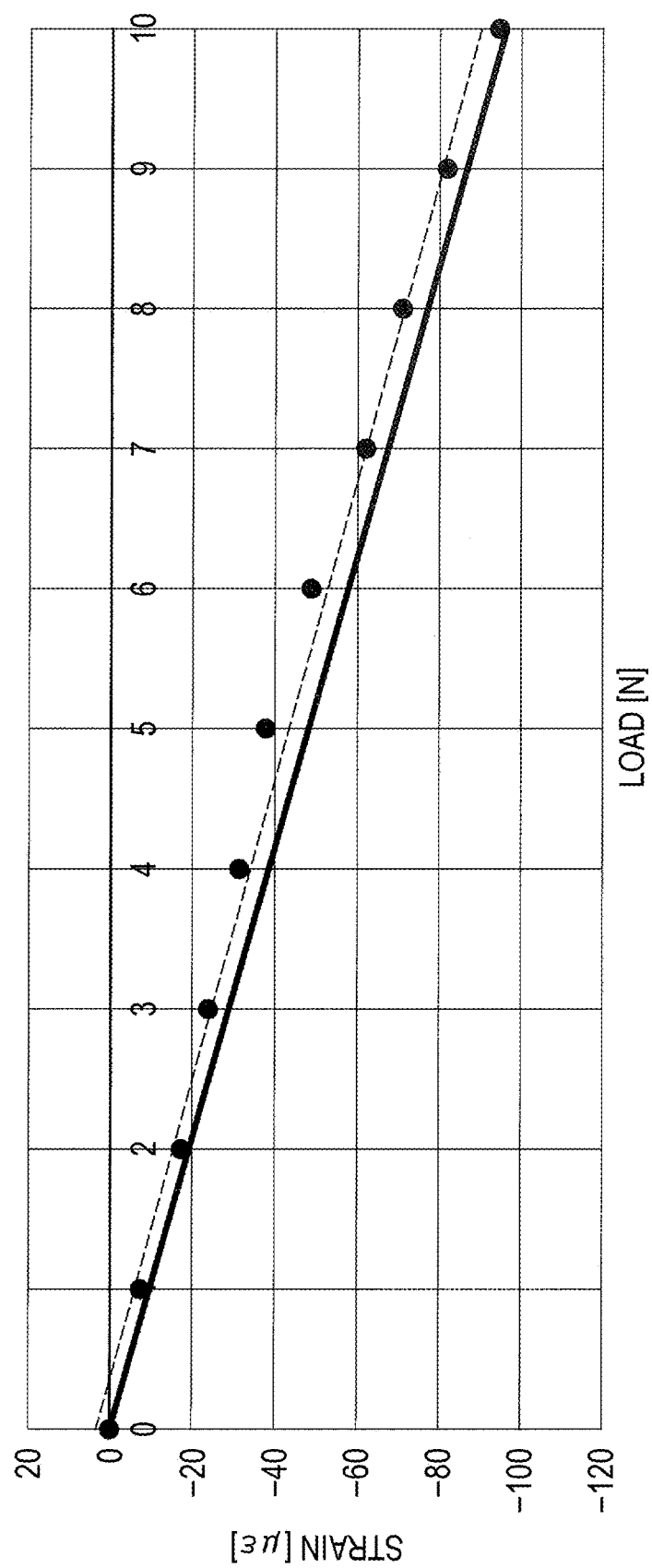
FIG. 28 is a graph illustrating results of an experimental example.

FIG. 28 illustrates measurement results in a case where the FBG sensors 51 to 54 are arranged as illustrated in FIG. 7, strain is measured for one of the sensors, and one FBG sensor is used for temperature compensation. The measurement was performed on a compression model of a cylindrical simple pipe shape. The cylindrical simple pipe shape has an inner diameter of 9 mm, an outer shape of 15 mm, and a sectional area of 113.1 mm$^2$. The material of the simple pipe is acrylic resin, and the Young's modulus thereof is 2,700 MPa. A load applied in the axial direction of the simple pipe is 0 N to 10 N.

The model of FBG sensor used in experiment is FOS-DTG-sensor. The optical fiber is LBL1550-125, has a total fiber length of 0.94 m and a fiber outer diameter of 190 μm (coated with a clad outer diameter of 125±1 µm), and is made of quartz glass. The number of FBG points is four, the FBG length is 2 mm, the FBG interval is 80 mm, and the tip end is 0.2 m. The optical fibers 51*f* to 54*f* were fixed at the first fixing points 51*p* to 54*p* and the second fixing points 51*q* to 54*q* by using the set screws 260 and the set pieces 261 illustrated in FIGS. 25A to 25C. Then, force was set to be applied only to the inner tube 21*b*. Theoretical values are indicated by a thick straight line in FIG. 28. As measured values (points indicated by black circles), values close to the theoretical values were obtained.

(5) Features (5-1)

The sensor-equipped hood 20 includes the hood main body 21 and the fiber Bragg grating sensor (FBG sensors) 50 to 55, 61, 71, 75. The hood main body 21 is transparent and has a tubular shape. The FBG sensor 50 to 55, 61, 71, 75 is fixed to the first fixing point 50*p* to 58*p* of the hood main body 21, and has the Bragg grating 50*b* to 58*b*, 61*b* to 68*b*, 71*b* to 78*b*.

In the FBG sensor 50 to 55, 61, 71, 75, the wavelength of the reflected light at the Bragg grating 50*b* to 58*b*, 61*b* to 68*b*, 71*b* to 78*b* changes based on fluctuation of the first fixing point 50*p* to 58*p* in the hood main body 21. The sensor-equipped hood 20 having such a configuration can detect fluctuation of the first fixing point 50*p* to 58*p* in the hood main body 21 by detecting the change in the wavelength of the reflected light at the FBG sensor 50 to 55, 61, 71, 75. The stress applied to the hood main body 21 can be detected from fluctuation of the first fixing point 50*p* to 58*p* while narrowing of an operating field obtained through the hood main body is reduced.

(5-2)

In the sensor-equipped hood 20, the FBG sensor 50 to 55 is fixed at the second fixing point 50*q* to 58*q* in the hood main body 21. The Bragg grating 50*b* to 58*b* is arranged between the first fixing point 50*p* to 58*p* and the second fixing point 50*q* to 58*q*. The wavelength of the reflected light at the Bragg grating 50*b* to 58*b* changes according to the change in the interval between the first fixing point 50*p* to 58*p* and the second fixing point 50*q* to 58*q*. As a result, in the sensor-equipped hood 20, the FBG sensor 50 to 55 can measure the stress which changes the interval between the first fixing point 50*p* to 58*p* and the second fixing point 50*q* to 58*q*.

(5-3)

In the sensor-equipped hood 20 illustrated in FIG. 7, the first fixing point 51*p* to 54*p* can be taken as the first point, the second fixing point 51*q* to 54*q* can be taken as a second point, and the Bragg grating 51*b* to 54*b* can be taken as the first Bragg grating. In the FBG sensor 51 to 54, the first point and the second point are arranged at the positions apart from each other in the axial direction of the hood main body 21, the first Bragg grating is arranged between the first point and the second point, and the wavelength of the reflected light at the first Bragg grating changes according to the change in the interval between the first point and the second point. The sensor-equipped hood 20 configured as described above can measure, by the FBG sensor 51 to 54, the stress applied between the first point and the second point in the axial direction of the hood main body 21, such as the compressive stress (see FIG. 5A) and the tensile stress (see FIG. 5B) in the axial direction of the hood main body.

(5-4)

In the sensor-equipped hood 20 illustrated in FIG. 7, the first fixing point 51*p* to 54*p* can be taken as the third point, the second fixing point 51*q* to 54*q* can be taken as the fourth point, and the Bragg grating 51*b* to 54*b* can be taken as the second Bragg grating. For example, the first fixing point 52*p* is taken as the third point, the second fixing point 52*q* is taken as the fourth point, the first fixing point 51*p* is taken as the first point, and the second fixing point 51*q* is taken as the second point. In this case, in the sensor-equipped hood 20, the third point (first fixing point 52*p*) and the fourth point (second fixing point 52*q*) are arranged apart from each other in the axial direction on the second straight line different from the first straight line connecting the first point (first fixing point 51*p*) and the second point (second fixing point 51*q*). In this case, the first Bragg grating (Bragg grating 51*b*) is arranged between the first point and the second point, and the second Bragg grating (Bragg grating 52*b*) is arranged between the third point and the fourth point. The wavelength of the reflected light at the first Bragg grating changes according to the change in the interval between the first point and the second point while the wavelength of the reflected light at the second Bragg grating changes according to the change in the interval between the third point and the fourth point. The sensor-equipped hood 20 can measure the stress applied between the first point (first fixing point 51*p*) and the second point (second fixing point 51*q*) in the axial direction of the hood main body 21 and strain at different locations between the third point (first fixing point 52*p*) and the fourth point (second fixing point 52*q*). In other words, for example, the bending stress applied to the hood main body 21 can be measured.

(5-5)

In the sensor-equipped hood 20 illustrated in FIG. 12, the first fixing point 55*p* to 58*p* can be taken as the fifth point, the second fixing point 55*q* to 58*q* can be taken as the sixth point, and the Bragg grating 55*b* to 58*b* can be taken as the third Bragg grating. In this case, in the FBG sensor 55, the fifth point (first fixing point 55*p* to 58*p*) and the sixth point (second fixing point 55*q* to 58*q*) are arranged at the positions apart from each other in the circumferential direction of the hood main body 21, the third Bragg grating (Bragg grating 55*b* to 58*b*) is arranged between the fifth point and the sixth point. The wavelength of the reflected light at the second Bragg grating changes according to the change in the interval between the third point and the fourth point, and the sensor-equipped hood 20 can measure the stress applied between the fifth point and the sixth point in the circumferential direction of the hood main body 21, such as the compressive stress (see FIG. 10A) and the tensile stress (see FIG. 10B) in the radial direction of the hood main body 21.

(5-6)

In the sensor-equipped hood 20 illustrated in FIG. 15A, for example, the first fixing point 72*p*, 73*p* can be taken as the fifth point, the second fixing point 72*q*, 73*q* can be taken as the sixth point, the Bragg grating 72*b*, 73*b* can be taken as the third Bragg grating, the first fixing point 76*p*, 77*p* can be taken as a seventh point, the second fixing point 76*q*, 77*q* can be taken as an eighth point, and the Bragg grating 76*b*, 77*b* can be taken as a fourth Bragg grating.

In the FBG sensor 71, the fifth point and the sixth point (first fixing point 72*p*, 73*p* and second fixing point 72*q*, 73*q*) are arranged at the positions apart from each other in the circumferential direction of the hood main body 21, the third Bragg grating (Bragg grating 72*b*, 73*b*) is arranged between the fifth point and the sixth point, and the wavelength of the reflected light at the third Bragg grating changes according to the change in the interval between the fifth point and the sixth point. In the FBG sensor 75, the seventh point and the eighth point (first fixing point 76p, 77p and second fixing point 76q, 77q) are arranged at the positions apart from each other in the circumferential direction of the hood main body, the fourth Bragg grating (Bragg grating 76b, 77b) is arranged between the seventh point and the eighth point, and the wavelength of the reflected light at the fourth Bragg grating changes according to the change in the interval between the seventh point and the eighth point.

The third Bragg grating (Bragg grating 72b, 73b) and the fourth Bragg grating (Bragg grating 76b, 77b) are arranged in a first optical fiber (optical fiber 71f) and a second optical fiber (optical fiber 75f) having different winding directions. The sensor-equipped hood 20 configured as described above can measure not only the stress applied between the fifth point and the sixth point in the circumferential direction of the hood main body 21 in the first optical fiber but also the stress applied between the seventh point and the eighth point in the circumferential direction of the hood main body 21 in the second optical fiber different from the first optical fiber in the winding direction, and can measure, for example, the force for twisting the hood main body 21.

(5-7)

In the FBG sensor 61 of the sensor-equipped hood 20 illustrated in FIGS. 14A and 14B, the plurality of Bragg gratings 61b to 68b are arranged in one optical fiber 61f, and the plurality of first fixing points (not illustrated) are arranged corresponding to the Bragg gratings 61b to 68b. In the sensor-equipped hood 20 configured as described above, the number of optical fibers 61f can be reduced while the number of measurement points is increased.

(5-8)

The FBG sensor 50, 51 of the sensor-equipped hood 20 is fitted in the groove 21f, 21g, the hole 21m, or the through-hole 21j formed in the hood main body 21, and is fixed to the first fixing point 51p by the pressure applied from the hood main body 21 to the FBG sensor. By removing the pressure applied to the FBG sensor 50, 51, the FBG sensor 50, 51 can be unfixed, and the hood main body 21 and the FBG sensor 50, 51 can be easily separated from each other. In addition, for example, the FBG sensor 50, 51 can be separated from the endoscope main body 1A together with the hood main body 21.

(5-9)

Figure 9A:
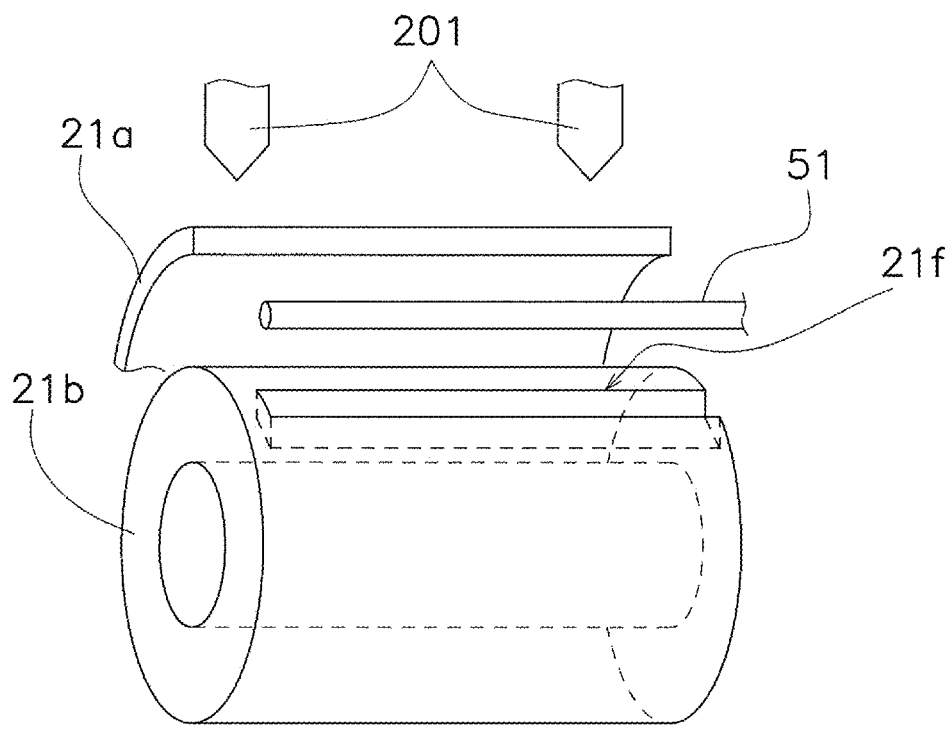
FIG. 9A is an exploded perspective view illustrating one example of a method of manufacturing the hood-equipped sensor.
Figure 9B:
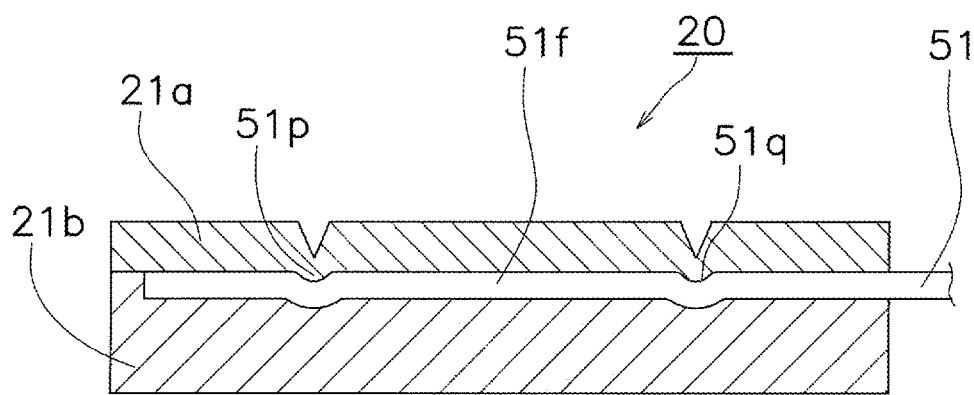
FIG. 9B is a partially enlarged sectional view for describing the method of manufacturing the hood-equipped sensor.

For example, the hood main body 21 of the sensor-equipped hood 20 illustrated in FIGS. 9A and 9B includes the outer tube 21a and the inner tube 21b which is an inner peripheral portion arranged in contact with the inside of the outer tube 21a. Such an FBG sensor 51 is arranged between the outer tube 21a and the inner tube 21b which is the inner peripheral portion. In the sensor-equipped hood 20 configured as described above, the FBG sensor 51 is easily attached to the hood main body 21 by using the outer tube 21a and the inner tube 21b (inner peripheral portion). Note that the inner peripheral portion is not necessarily the inner tube 21b, and for example, may be a rounded plate-shaped member having elasticity instead of the inner tube 21b.

Although one embodiment of the present invention has been described above, the present invention is not limited to the above-described embodiment and various changes can be made without departing from the gist of the invention. In particular, the plurality of embodiments and modifications described in the present specification can be arbitrarily combined as necessary.

LIST OF REFERENCE CHARACTERS

1 Endoscope
1A Endoscope Main Body
20 Hood-Equipped Sensor
21 Hood Main Body
21a Outer Tube
21b Inner Tube (Example of Inner Peripheral Portion)
21f, 21g Groove
21m Hole
21j Through-Hole
50 to 55, 61, 71, 75 FBG Sensor
50f to 55, 61, 71, 75 Optical Fiber
51b to 58b, 51t, 61b to 68b, 71b to 78b Bragg Grating
51p to 58p, 71p to 78p First Fixing Point
51q to 58q, 71q to 78q Second Fixing Point

The invention claimed is:

1. A sensor-equipped hood configured to protrude from a tip end portion of an endoscope main body and attach to the tip end portion, comprising:
a hood main body that is transparent and tubular; and
a fiber Bragg grating sensor fixed to at least one first fixing point of the hood main body and having at least one Bragg grating, wherein
the hood main body includes a configured to protude portion protruding from the tip end portion of the endoscope main body and an attachment portion configured to attach to the tip end portion of the endoscope main body,
the at least one Bragg grating is arranged at the protruding portion of the hood main body, and
the fiber Bragg grating sensor is configured to change a wavelength of reflected light at the at least one Bragg grating based on fluctuation of the at least one first fixing point in the hood main body.

2. The sensor-equipped hood according to claim 1, wherein
the fiber Bragg grating sensor is also fixed at at least one second fixing point in the hood main body, the at least one Bragg grating is arranged between the at least one first fixing point and the at least one second fixing point, and the wavelength of the reflected light at the at least one Bragg grating changes according to a change in an interval between the at least one first fixing point and the at least one second fixing point.

3. The sensor-equipped hood according to claim 2, wherein
the at least one first fixing point includes a first point, the at least one second fixing point includes a second point, and the at least one Bragg grating includes a first Bragg grating, and
in the fiber Bragg grating sensor, the first point and the second point are arranged at positions apart from each other in an axial direction of the hood main body, the first Bragg grating is arranged between the first point and the second point, and a wavelength of reflected light at the first Bragg grating changes according to a change in an interval between the first point and the second point.

4. The sensor-equipped hood according to claim 3, wherein
the at least one first fixing point includes a third point, the at least one second fixing point includes a fourth point, and the at least one Bragg grating includes a second Bragg grating, and
in the fiber Bragg grating sensor, the third point and the fourth point are arranged apart from each other in the axial direction on a second straight line different from a first straight line connecting the first point and the second point, the second Bragg grating is arranged between the third point and the fourth point, and a wavelength of reflected light at the second Bragg grating changes according to a change in an interval between the third point and the fourth point.

5. The sensor-equipped hood according to claim 2, wherein the first fixing point includes a fifth point, the second fixing point includes a sixth point, and the at least one Bragg grating includes a third Bragg grating, and in the fiber Bragg grating sensor, the fifth point and the sixth point are arranged at positions apart from each other in a circumferential direction of the hood main body, the third Bragg grating is arranged between the fifth point and the sixth point, and a wavelength of reflected light at the third Bragg grating changes according to a change in an interval between the fifth point and the sixth point.

6. The sensor-equipped hood according to claim 5, wherein the at least one first fixing point includes a seventh point, the at least one second fixing point includes an eighth point, and the at least one Bragg grating includes a fourth Bragg grating, and in the fiber Bragg grating sensor, the seventh point and the eighth point are arranged at positions apart from each other in the circumferential direction of the hood main body, the fourth Bragg grating is arranged between the seventh point and the eighth point, a wavelength of reflected light at the fourth Bragg grating changes according to a change in an interval between the seventh point and the eighth point, and the third Bragg grating and the fourth Bragg grating are arranged in a first optical fiber and a second optical fiber different from each other in a winding direction.

7. The sensor-equipped hood according to claim 1, wherein in the fiber Bragg grating sensor, the at least one Bragg gratings include a plurality of Bragg gratings arranged in one optical fiber, and the at least one first fixing points include a plurality of first fixing points arranged corresponding to the plurality of Bragg gratings.

8. The sensor-equipped hood according to claim 1, wherein the fiber Bragg grating sensor is fitted in a hole or a groove formed in the hood main body, and is fixed to the at least one first fixing point by pressure applied from the hood main body to the fiber Bragg grating sensor.

9. The sensor-equipped hood according to claim 1, wherein the hood main body includes an outer tube and an inner peripheral portion arranged in contact with an inside of the outer tube, and the fiber Bragg grating sensor is arranged between the outer tube and the inner peripheral portion.

10. An endoscope comprising:

an endoscope main body;

a hood main body that is transparent, tubular, and attached to a tip end portion of the endoscope main body;

a fiber Bragg grating sensor fixed to a first fixing point of the hood main body and having a Bragg grating; and an interrogator that is configured to measure stress related to fluctuation of the first fixing point in the hood main body by reflected light at the Bragg grating of the fiber Bragg grating sensor, wherein the hood main body includes a protruding portion protruding from the tip end portion and an attachment portion attached to the tip end portion, and the Bragg grating is arranged at the protruding portion of the hood main body.

11. The sensor-equipped hood according to claim 1, wherein the fiber Bragg grating sensor is fitted in a hole or a groove formed in the hood main body, and is fixed to the at least one first fixing point by an adhesive.

* * * * *